US012796757B2

(12) United States Patent
Bäck et al.

(10) Patent No.: US 12,796,757 B2
(45) Date of Patent: Nov. 17, 2026

(54) PANT-TYPE GARMENT AND METHOD FOR THE PRODUCTION THEREOF

(71) Applicant: Essity Hygiene and Health Aktiebolag, Gothenburg (SE)

(72) Inventors: Lucas Bäck, Gothenburg (SE); Victor Oredsson, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 504 days.

(21) Appl. No.: 17/770,793

(22) PCT Filed: Oct. 22, 2019

(86) PCT No.: PCT/SE2019/051037

§ 371 (c)(1),
(2) Date: Apr. 21, 2022

(87) PCT Pub. No.: WO2021/080477

PCT Pub. Date: Apr. 29, 2021

(65) Prior Publication Data

US 2022/0386723 A1 Dec. 8, 2022

(51) Int. Cl.
*A41D 27/24* (2006.01)
*A61F 13/72* (2006.01)
*A61F 13/80* (2006.01)

(52) U.S. Cl.
CPC .............. *A41D 27/24* (2013.01); *A61F 13/72* (2013.01); *A61F 13/80* (2013.01)

(58) Field of Classification Search
CPC ......... A41D 27/24; A61F 13/72; A61F 13/80; A61F 13/15739; A61F 13/49011; A61F 13/4963
See application file for complete search history.

(56) References Cited

U.S. PATENT DOCUMENTS 4,115,683 A 9/1978 Clark et al.
5,236,430 A 8/1993 Bridges
(Continued)

FOREIGN PATENT DOCUMENTS

CN 101448477 A 6/2009
CN 101568314 A 10/2009
(Continued)

OTHER PUBLICATIONS

Office Action (Notice of Reasons for Rejection) issued on Apr. 3, 2023, in corresponding Japanese Patent Application No. 2022-522050 and English translation of the Office Action. (8 pages).
(Continued)

*Primary Examiner* — Rebecca E Eisenberg
*Assistant Examiner* — Kate Elizabeth Strachan
(74) *Attorney, Agent, or Firm* — Buchanan Ingersoll & Rooney PC

(57) ABSTRACT

The front and back portions are joined in a first and a second side seam along opposing side edges of the front and back portions and comprising a stretch-bonded laminate web including an elastic film which is stretch-bonded between two nonwoven webs. The side seams are constituted by fusion bonds formed by laser bonding and extend along the side edges of the front and back portions of the pant-type garment. The side seams have a width in the width direction of the pant-type garment in the range of from 0.3 to 1.5 millimetres, and a thickness in the range of from 0.2 to 1.5 millimeters, the thickness of the side seams being perpendicular to the width direction and the length direction of the pant type garment.

23 Claims, 9 Drawing Sheets

(56) References Cited

U.S. PATENT DOCUMENTS

| | | | |
|---|---|---|---|
| 6,394,991 B1 | 5/2002 | Takei et al. | |
| 8,282,616 B2 | 10/2012 | Lehto et al. | |
| 10,166,153 B2 | 1/2019 | Wågdahl | |
| 11,000,427 B2 | 5/2021 | Eriksson et al. | |
| 11,051,997 B2 | 7/2021 | Bäck et al. | |
| 2006/0283846 A1 | 12/2006 | Lupinetti et al. | |
| 2010/0063468 A1* | 3/2010 | Lehto | A61F 13/4963 156/227 |
| 2014/0110037 A1 | 4/2014 | Verboomen et al. | |
| 2015/0144251 A1 | 5/2015 | Schoultz et al. | |
| 2016/0083898 A1 | 3/2016 | Godmaire et al. | |
| 2016/0120709 A1 | 5/2016 | Hamamoto et al. | |
| 2016/0250082 A1 | 9/2016 | Hamamoto et al. | |
| 2017/0216105 A1* | 8/2017 | Bäck | A61F 13/49413 |
| 2017/0266055 A1 | 9/2017 | Schneider et al. | |
| 2018/0021186 A1* | 1/2018 | Wågdahl | B32B 27/40 604/385.16 |
| 2019/0262189 A1 | 8/2019 | Bäck | |
| 2022/0370264 A1 | 11/2022 | Bäck et al. | |

FOREIGN PATENT DOCUMENTS

| | | | | |
|---|---|---|---|---|
| CN | 103876897 | A | 6/2014 | |
| CN | 104394821 | A | 3/2015 | |
| CN | 105246442 | A | 1/2016 | |
| CN | 105307616 | A | 2/2016 | |
| CN | 105358110 | A | 2/2016 | |
| CN | 105682628 | A | 6/2016 | |
| CN | 107205870 | A | 9/2017 | |
| CN | 108135756 | A | 6/2018 | |
| CN | 110022815 | A | 7/2019 | |
| CN | 110337285 | A | 10/2019 | |
| EP | 0613363 | B1 | 7/1997 | |
| EP | 2258639 | A1 | 12/2010 | |
| EP | 2813347 | A1 | 12/2014 | |
| EP | 3015096 | A1 | 5/2016 | |
| EP | 3064182 | A1 | 9/2016 | |
| EP | 3260095 | B1 | 10/2018 | |
| JP | 2010115849 | A | 5/2010 | |
| JP | 2010188629 | A | 9/2010 | |
| JP | 2011125641 | A | 6/2011 | |
| JP | 2011126011 | A | 6/2011 | |
| JP | 2013043292 | A | 3/2013 | |
| JP | 2013071282 | A | 4/2013 | |
| JP | 2013146549 | A | 8/2013 | |
| JP | 2013256133 | A | 12/2013 | |
| JP | 2015008946 | A | 1/2015 | |
| JP | 2015008947 | A | 1/2015 | |
| JP | 2015008948 | A | 1/2015 | |
| JP | 2015008950 | A | 1/2015 | |
| JP | 2015009505 | A | 1/2015 | |
| JP | 2015027779 | A | 2/2015 | |
| JP | 2015085087 | A | 5/2015 | |
| JP | 2015085088 | A | 5/2015 | |
| JP | 2015085653 | A | 5/2015 | |
| JP | 2015085654 | A | 5/2015 | |
| JP | 2015112399 | A | 6/2015 | |
| JP | 2016078335 | A | 5/2016 | |
| JP | 2016097511 | A | 5/2016 | |
| JP | 2016097611 | A | 5/2016 | |
| JP | 2016112166 | A | 6/2016 | |
| JP | 2016115829 | A | 6/2016 | |
| JP | 2016154996 | A | 9/2016 | |
| JP | 2016158799 | A | 9/2016 | |
| JP | 2017148111 | A | 8/2017 | |
| JP | 2018139718 | A | 9/2018 | |
| WO | 2007138373 | A1 | 12/2007 | |
| WO | 2008015550 | A2 | 2/2008 | |
| WO | 2008081239 | A2 | 7/2008 | |
| WO | 2008154093 | A1 | 12/2008 | |
| WO | 2012070462 | A1 | 5/2012 | |
| WO | 2012114295 | A1 | 8/2012 | |
| WO | 2014103818 | A1 | 7/2014 | |
| WO | 2014136904 | A1 | 9/2014 | |
| WO | 2014183210 | A1 | 11/2014 | |
| WO | 2014208635 | A1 | 12/2014 | |
| WO | 2014208636 | A1 | 12/2014 | |
| WO | 2014208637 | A1 | 12/2014 | |
| WO | 2014208639 | A1 | 12/2014 | |
| WO | 2014208640 | A1 | 12/2014 | |
| WO | 2014208641 | A1 | 12/2014 | |
| WO | 2014208642 | A1 | 12/2014 | |
| WO | 2014208650 | A1 | 12/2014 | |
| WO | 2014208652 | A1 | 12/2014 | |
| WO | WO-2014208651 | A1 * | 12/2014 | A61F 13/15739 |
| WO | 2015059204 | A2 | 4/2015 | |
| WO | 2015064303 | A1 | 5/2015 | |
| WO | 2015064405 | A1 | 5/2015 | |
| WO | 2015064418 | A1 | 5/2015 | |
| WO | 2015064606 | A1 | 5/2015 | |
| WO | 2015153993 | A1 | 10/2015 | |
| WO | 2015159207 | A1 | 10/2015 | |
| WO | 2016002667 | A1 | 1/2016 | |
| WO | 2016073819 | A1 | 5/2016 | |
| WO | 2016098521 | A1 | 6/2016 | |
| WO | 2016132645 | A1 | 8/2016 | |
| WO | 2019039981 | A1 | 2/2019 | |
| WO | 2021080475 | A1 | 4/2021 | |

OTHER PUBLICATIONS

Notification of the First Office Action issued on Aug. 10, 2022, by the Chinese Patent Office in corresponding Chinese Patent Application No. 201980101612.0, and an English Translation of the Office Action. (16 pages).

Notification of the First Office Action issued on Aug. 10, 2022, by the Chinese Patent Office in corresponding Chinese Patent Application No. 201980101616.9, and an English Translation of the Office Action. (17 pages).

Office Action (Decision of Rejection) issued on Aug. 21, 2023, in corresponding Japanese Patent Application No. 2022-523986 and English translation of the Office Action. (4 pages).

International Search Report (PCT/ISA/210) and Written Opinion (PCT/ISA/237) mailed on Jun. 26, 2020, by the Swedish Patent Office as the International Searching Authority for International Application No. PCT/SE2019/051035. (14 pages).

International Search Report (PCT/ISA/210) and Written Opinion (PCT/ISA/237) mailed on Jun. 30, 2020, by the Swedish Patent Office as the International Searching Authority for International Application No. PCT/SE2019/051036. (13 pages).

International Search Report (PCT/ISA/210) and Written Opinion (PCT/ISA/237) mailed on Jun. 30, 2020, by the Swedish Patent Office as the International Searching Authority for International Application No. PCT/SE2019/051037. (14 pages).

English language of the Search Report/Written Opinion issued on Nov. 30, 2023, in corresponding Brazilian Patent Application No. BR112022006130-7. (4 pages).

Extended European Search Report dated Jun. 5, 2023, issued in corresponding European Application No. 19950146.1. (8 pages).

Office Action (Notice of Reasons for Rejection issued on Oct. 16, 2023, in corresponding Japanese Patent Application No. 2022-522050 and English translation of the Office Action. (9 pages).

Office Action (Notice of Allowance) issued on Jul. 2, 2025, by the U.S. Patent and Trademark Office in co-pending U.S. Appl. No. 17/770,865. (8 pages).

* cited by examiner

PANT-TYPE GARMENT AND METHOD FOR THE PRODUCTION THEREOF

TECHNICAL FIELD

The invention pertains to a pant-type garment having a length direction and a width direction. The pant-type garment is divided in the length direction into a front portion, a back portion and a crotch portion located between the front portion and the back portion. The front portion and the back portion each has a waist edge extending in the width direction and a pair of opposing side edges extending in the longitudinal direction. The front and back portions are joined by fusion bonds forming side seams along the opposing side edges.

BACKGROUND

In particular for adult wearers of disposable pant-type garments such as pant diapers, sanitary pants, swimwear, and incontinence pants it is important that the garments as closely as possible resemble ordinary underwear and that they are not perceived as being "diapers". Hence, pant-type garments such as pant diapers, sanitary pants, swimwear, and incontinence pants are designed to fit comfortably and snugly about the wearer. It is also desirable that the garments have a tailored and neat appearance, and that they can be inconspicuously worn beneath ordinary clothing. The garments are commonly made by production methods involving feeding one or more continuous webs of cover material in a machine direction and attaching other components of the garments such as elastic elements, absorbent cores, etc. to the continuous web or webs to form a precursor web of interconnected pant-type garments. The pant-type garments are arranged with a longitudinal direction of the pant-type garments aligned with a cross machine direction of the precursor web, perpendicular to the machine direction. The precursor web is provided with leg openings which are formed between the interconnected pant-type garments. Individual pant-type garments are formed by folding the precursor web in the machine direction, joining the superposed layers of the precursor web to form side seams and severing individual pant-type garments from the continuous precursor web, such as by cutting.

The side seams of conventional pant-type garments are generally band-shaped joins which are formed by ultrasonic welding or thermowelding. In order to have sufficient strength to withstand the forces to which the pant-type garment is exposed during donning of the garment and to allow sufficient production tolerances when cutting off individual pant-type garments from a precursor web, such side seams need to be relatively broad, in the order of 5 to 10 millimetres, or more. The side seams protrude from the side edges of the pant-type garment and are one of the most visible differences between textile underwear and a disposable pant-type garment, giving the disposable pant-type garment a non-appealing, low quality appearance. Furthermore, such side seams are bulky and difficult to hide beneath tight-fitting clothes.

Furthermore, it is a desire that a soiled pant-type garment can be easily removed without having to pull the garment down over the legs of a user. Therefore, the side seams should be breakable by manual force to allow a user or a caregiver to pull apart the side seams before removing a soiled pant-type garment. A problem which is encountered with the traditional broad side seams is to achieve a good balance in the strength properties, such that the side seams do not break by the forces arising during donning and normal use, but still can be easily broken by manual force for removal of the garment after use.

In EP2 813 347 A1 and EP3 064 182 A1 laser welding has been suggested as a means for forming narrow side seams and sever individual pant-type garments from a precursor web in a single operation.

An object of the present disclosure is to offer a pant-type garment having side seams having further improved functionality and being inconspicuous.

SUMMARY

One or more of the above objects may be achieved with a pant-type garment in accordance with claim 1. Further embodiments are set out in the dependent claims, in the following description and in the drawings.

Disclosed herein is a pant-type garment having a length direction and a width direction and being divided in the length direction into a front portion, a back portion and a crotch portion located between the front portion and the back portion, the front portion having a front waist edge extending in the width direction and a pair of opposing side edges extending in the longitudinal direction and the back portion having a back waist edge extending in the width direction and a pair of opposing side edges extending in the longitudinal direction, the front and back portions being joined in a first and a second side seam arranged in first and second side seam regions formed by superposed layers of the front and back portions along the opposing side edges of the front and back portions, the first and second side seam regions comprising thermoplastic web material, the side seams being constituted by fused thermoplastic material extending along the side edges of the front and back portions of the pant-type garment. Each of the side seams has a width in the width direction of the pant-type garment in the range of from 0.3 to 1.5 millimetres, and a thickness in the range of from 0.2 to 1.5 millimeters, the thickness of the side seam being perpendicular to the width direction and the length direction of the pant type garment and in that the material of the front and back portions comprises or consists of an elastic laminate comprising an elastic film which is stretch-bonded between two outer nonwoven webs, the side seams being fully or partly formed in the elastic laminate web.

As set out herein the front and back portions are joined in a first and a second side seam, the side seams being fully or partly formed by superposed layers of the front and back portions arranged along opposing side edges of the front and back portions and at least partly comprising the stretch bonded elastic laminate. The fused side seams are formed by laser bonding and have a narrow width and a small thickness.

Stretch bonding means bonding of a non-elastic or less elastic layer to an elastic material while the elastic material is stretched at least 50% in at least one direction.

The elastic laminate has a material thickness and a ratio $t_s/t_m$ between the thickness $t_s$ of the side seam and the material thickness $t_m$ is in the range of from 1.0 to 1.3, such as from 1.1 to 1.3 or from 1.1 to 1.2. The thickness ratio is determined under tension with the materials stretched out perpendicular to the longitudinal direction of the side seam, according to the method as disclosed herein.

A thickness ratio within the above ranges indicates that the side seams have a thickness which is slightly greater or in the same order as the adjoining web material, when measured with the article in a stretched state according to the method, as disclosed herein. Even if the side seams protrude slightly from the surface of the stretch-bonded laminate web they are inconspicuous and give the pant-type garment a neat and seam-less appearance closely resembling ordinary textile underpants. In a pant-type garment as set out herein, the fused side seams are preferably located on a garment facing surface of the pant-type garment.

When the stretch-bonded laminate is in a relaxed state or in a not fully stretched state which is the case when the pant-type garment is taken out of a package and normally also when it is being worn, the non-elastic or less elastic web or webs which are bonded to the elastic material is contracted by the elastic material causing rugosities to be formed in the non-elastic or less elastic web or webs. During use of the pant-type garment, such rugosities serve to visually conceal and obscure the fused side seams and to provide tactile shielding of the fused material in the side seams which is generally harder and stiffer than adjoining web material. In the pant-type garment as disclosed herein, the fused and consolidated material in the side seams is preferably located on the outside of the pant-type garment, such that the inner surface retains the properties of the non-fused web material and remains smooth and soft. As set out herein, when the pant-type garment is fully extended perpendicular to the side seam, the side seam may have a thickness causing it to protrude somewhat from the surface of the adjoining materials. A thicker side seam may be desired in order to provide increased strength of the side seam. The protruding side seam is preferably located on the garment facing side of the pant-type garment in order to provide the increased strength while retaining a soft and smooth inside. As set out herein, the consolidated material in the side seam has a slightly greater thickness or an equal thickness than the adjoining materials when stretched according to the method as disclosed herein.

At least one and preferably both of the non-woven webs in the stretch-bonded laminate web may be bonded to the elastic film by means of discrete bonding elements, such as line bonds or point bonds. By using discrete bonding elements arranged in a bonding pattern, the relaxed and gathered nonwoven webs may be caused to pucker in a controlled and regular way in the non-bonded portions between the bonds. Such controlled puckering of the nonwoven webs provides the elastic laminate web with high-loft, soft and airy cushioning outer layers having a functional thickness which is considerably greater than the thickness of the non-gathered nonwoven webs. The bonding pattern may be selected to provide the laminate web with a regular appearance, e.g. a point bonding pattern which causes the nonwoven web or webs to gather in a way resembling a woven web. The discrete bonds may be created e.g. by thermo-bonding or by ultrasonic bonding, with ultrasonic bonding being preferred, as disclosed herein. A particularly suitable bonding pattern may be a pattern of off-set point bonds. It may be particularly preferred that the elastic film layer is a non-thermoplastic film and the nonwoven layers are thermoplastic layers or at least predominantly thermoplastic layers and that bonding of the elastic film layer between the nonwoven web layers is carried out by simultaneously perforating the elastic film layer and create fusion bonds between the nonwoven web layers at the perforations in the elastic film layer. An elastic laminate which has been made in this way has excellent breathability and is highly suitable for use as an outer cover in a pant-type garment as disclosed herein.

The elastic film may be absent in parts of the laminate web such as in a crotch portion of the pant-type garment. The elastic film is preferably a non-thermoplastic elastic film, which is severed when forming the side seams by laser welding. As the elastic film is held under tension during side seam formation, the severed elastic film will spring back from the side seam causing a non-elastic area to be created along each of the side seams, the non-elastic area having a width on each side of the side seam of from 0.7 millimetres to 20 millimetres, such as from 0.9 millimetres to 5 millimetres. It is to be understood that residues of the film may remain in the fused material of the side seam itself.

The side seams are constituted by of strips of fused material which constitute the full sealed area of a side seam and extend in the longitudinal direction of the pant-type garment. Each side seam may have a generally rectangular cross-sectional area along all or part of the length of the side seam in the longitudinal direction of the pant-type garment. A generally rectangular cross-sectional area of the fused side seams as disclosed herein may also be referred to as the cross-sectional area of the fused side seam having a box-shape. By characterizing the cross-sectional area of the side seams as being “generally rectangular”, slight variations in the cross-sectional shape which may occur when producing the side seams are taken into account. Accordingly, by a generally rectangular or box-shaped cross-sectional area is implied a cross-sectional area which may deviate slightly from a perfect rectangular cross-sectional shape, e.g. by having rounded corners and/or one or more side edge which may deviate slightly from a straight line. However, the overall appearance of the generally rectangular or box-shaped cross-sectional area is that of a rectangular shape, including a square shape. Such cross-sectional shape has been found to provide reliable side seams with uniform strength properties. Box-shaped side seams have been found to be sufficiently strong to prevent failure when pulling out the pant in the width direction during donning of the pant. As the side seams are very narrow and thin, they are still easy to break by tearing along the side seams in the longitudinal direction. Thus, the pant-type garment as disclosed herein can be readily torn open for easy removal after use.

Each side seam may have a generally rectangular cross-sectional area along the full length of the side seam or along only a part of the side seam. It may be preferred that each side seam has a rectangular cross-sectional area along a major part of the side seam, such as along 60% to 100% of the side seam or along 80% to 100% of the side seam.

The box-shape of the cross-sectional area is at least partly attributed to the material involved in forming the fused side seams being stretched in the machine direction during welding. The side seams are formed while holding the webs in the front and back portions of the pant-type garment closely pressed together along the side seams, which produces distinct, durable and well defined side seams and which further contributes to obtaining side seams with a box-shaped cross-sectional area.

A ratio of the width of the fused side seam to the thickness of the side seam may be in the range of from 0.7 to 1.5, such as from 0.9 to 1.2.

The side seams of the pant-type garment as disclosed herein are arranged in side seam regions, which are the parts of the pant-type garment which during use are placed over the hips of a user and which extend between the waist opening of the pant-type garment to a corresponding one of the leg openings of the pant-type garment. As set out herein, the pant-type garment comprises or consists of superposed webs within the areas of the side seams. The fused side seams are preferably located on a garment facing surface of the pant-type garment.

The fused side seams may be formed in any suitable elastic laminate web material containing a sufficient amount of thermoplastic material to provide functional side seams. The nonwoven webs in the laminate may be fully or at least predominantly formed from thermoplastic polymers. The elastic film may be a thermoplastic film, although non-thermoplastic films may be preferred, as set out herein. In the pant-type garment such laminate webs may form part of or constitute components such as an inner liner, an acquisition layer, a side flap a waist feature or an outer cover. The thermoplastic material in the areas of the side seams may, for instance, comprise or consist of polypropylene and/or polyethylene. It may be preferred that the side seams are at least partly formed in a cover web. The cover web may form all or part of an outer cover of the pant-type garment.

A stretch-bonded elastic laminate having outer fibrous nonwoven layers is highly suitable for being arranged as an outside coversheet material as well as an inner coversheet material over at least part of the front panel and/or the back panel and may also be present in the crotch portion of the pant-type garments as disclosed herein. Alternatively, the crotch portion of a pant-type garment as disclosed herein may be inelastic or may be less elastic than the front and back panels.

It may be preferred that the stretchbonded elastic laminate constitutes the coversheet material over a major part of one or both of the front panel and the back panel, such as 60% to 100% of one or both of the front panel and the back panel or 80% to 100% of the front panel and the back panel.

Stretch bonding means bonding one or more non-elastic or less elastic layer or layers to an elastic material while the elastic material is stretched at least 50%. A stretch-bonded elastic laminate may constitute the sole component of an outer cover of the pant-type garment in at least 20%, preferably at least 25%, more preferably at least 30% and most preferably at least 40% of the total surface area of the pant-type garment, as seen in a flat state. The elastic film is preferably intermittently bonded to the non-elastic or less elastic layer or layers such that some portions of the elastic film are free from bonds to the non-elastic or less elastic layer or layers.

As set out herein, the stretch bonded laminate may be a laminate of an elastic film which is sandwiched between and bonded to two outer nonwoven webs. The elastic film may be elastic in one or more directions and at least one and preferably both of the outer nonwoven webs are made from thermoplastic fibres. The nonwoven webs may be of any suitable type, as disclosed herein. The elastic film is bonded to the outer nonwoven webs while being stretched to at least 50% elongation in at least one direction. The film may be stretched to at least 50% elongation in the machine direction and the stretchbonded laminate may be incorporated into a pant-type garment as disclosed herein with the machine direction coinciding with the width direction of the pant-type garment. The elastic film may be intermittently bonded between the outer nonwoven webs with a bonding pattern comprising discrete bonding elements such as bond points. The bonded area may be from 3% to 20%, such as from 3% to 15% or from 4% to 10%. A preferred bonding method may be ultrasonic bonding. Ultrasonic bonding may create apertures in the elastic film at the bond elements, which may enhance breathability of the elastic laminate.

As set out herein, the fused side seams of a pant-type garment as disclosed herein are formed while keeping the elastic film stretched in a direction perpendicular to the side seam. The heat which is applied to the materials at the side seam causes the elastic film to become severed along the side seams and to retract somewhat from the side seams. Thereby, the elastic film will be absent or at least partially absent in a band-shaped area along the side seams. The extent of the snap-back from the side seams is largely determined by the bonding pattern of the elastic laminate. When using a bonding pattern comprising discrete bonding elements such as bond points and having a bonded area as measured in an extended state of the laminate of from 3% to 20%, such as from 3% to 15% or from 4% to 10%, the elastic film will be retracted by 0.7 millimetres to 20 millimetres, such as from 0.9 millimetres to 5 millimetres from each side seam on either side thereof along most of its length, such as along 60% to 100% of the length of the side seam. The elastic-free areas in the vicinity of the side seams increases breathability along the side seams and reduces wearing pressure on the hips of a wearer of the pant-type garment.

It is to be understood that residues of the film may remain in the side seam and may be entrapped in the strip of fused thermoplastic material forming the side seam.

The elastic film is arranged to provide elasticity to the pant-type garments in the width direction of the garments, which corresponds to the machine direction in the method as disclosed herein. In addition, the elastic film may be arranged to provide elasticity to the pant-type garments in the longitudinal direction of the garments, corresponding to the cross machine direction in the method as disclosed herein.

The nonwoven webs used in the pant-type garment as disclosed herein may be spunbond, air laid, wet laid, carded, electro spun, meltblown or multi-layer nonwovens such as SMS (spunbond-meltblown-spunbond) nonwovens etc. The nonwoven web may be bonded by any suitable technique or combination of techniques, such as needling, hydroentangling, ultrasonic welding and thermobonding. It may be preferred that at least one of the nonwoven webs involved in forming the fused side seams of a pant-type garment as disclosed herein comprises at least one spunbond layer and optionally at least one meltblown layer. The nonwoven webs contain at least a functional amount of thermoplastic fibres, such as mono-component, bi-component and multicomponent fibres of polymers such as polyolefins, polyesters, etc. The thermoplastic fibres are preferably present in an amount of at least 50% by weight of the nonwoven web, such as at least 70% by weight of the nonwoven web or at least 80% by weight of the nonwoven web. The fibres may include non-thermoplastic fibres such as regenerated fibres such as viscose fibres and modal fibres and natural fibres such as cellulose pulp fibres, cotton fibres, flax, hemp, etc.

A cover web as disclosed herein may be a single unitary cover web comprising a front panel portion, a back panel portion and a crotch portion between the front panel portion and the back panel portion.

Alternatively the cover web may comprise a front panel web and a back panel web with the front panel web and the back panel web being separate webs and being joined by a crotch material. As set out herein, the crotch material may be generally non-elastic or may be an elastic material which is less elastic than the front and back panel webs. The crotch material may include an absorbent core and components such as a backsheet, a topsheet and elastic elements, such as leg elastic elements.

The pant-type garment as disclosed herein may comprise a waist elastic feature extending along all or part of one or both of the front waist edge and the back waist edge. The waist elastic feature may be formed as a part of an elastic cover web which is also present in the front portion and/or the back portion of the pant-type garment such that the waist elastic feature is an integral part of the cover web. A further option is to supplement the elastic material in an elastic cover by arranging additional waist elastic along the edges. The waist elastic can be supplied as bands, film, threads, etc., as known in the art and is preferably attached along the front and back waist edges of the pant-type garment in a tensioned state so as to create higher elastic tension at the waist edges. The waist elastic may be covered or uncovered as desired. If the waist elastic is covered by a further material, the covering material may be provided as a folded over part of one or more layers of a cover web or may be covered by a separate strip of material such as a nonwoven web. A waist elastic feature may further be applied as a separate prefabricated waistband component which is attached along a waist edge of a cover web.

Side seams having a generally rectangular or box-shaped cross-sectional area as disclosed herein may be formed by a method for simultaneously forming side seams and severing individual pant-type garments from a precursor web of interconnected pant-type garments, the method involving pressing the precursor web while the precursor web is being held in a stretched state against an outer support surface of a rotating support roll within pressing areas arranged along opposite longitudinal sides of a side seam area of a leading and a trailing pant-type garment. The precursor web is stretched at least in the machine direction, which is coincident with the rotational direction of the support roll and with a width direction of the pant-type garments in the precursor web. The pressing is carried out with a pressing arrangement comprising a laser beam passage which is applied to the precursor web with the laser beam passage in registry with and overlying the side seam area.

The side seams are formed simultaneously with severing individual pant-type garments from the precursor web by means of a laser beam generated by a laser unit arranged outside of the support roll. The laser beam is directed onto the precursor web through the laser beam passage and is controlled to move along the laser beam passage in the cross machine direction and in the machine direction in synchrony with rotation of the support roll and to keep a position of a focus point of the laser beam at a constant distance from the support surface throughout the welding and severing procedure.

After the side seams have been formed they are cooled while maintaining pressure on the pressure areas along the side seams until the welded and severed individual pant-type garments have been moved to a take-off section of the support roll where the pressure is released and the individual pant-type garments are removed from the support roll.

The method may include the steps of:

feeding the precursor web in a machine direction onto a support surface at a lay-down position on an outer periphery of a rotating support roll, the precursor web being stretched in the machine direction and optionally in a cross machine direction, perpendicular to the machine direction;

pressing the precursor web against the support surface within pressing areas arranged on opposite sides of a side seam area of a leading and a trailing individual pant-type garment, as seen in the machine direction;

forming side seams in the precursor web and simultaneously severing individual pant-type garments from the precursor web by applying energy to the precursor web by means of a laser beam to locally melt and fuse thermoplastic material in superposed layers of the precursor web within the side seam area, the laser beam being directed onto the precursor web from outside the support roll through and along a laser beam passage, the laser beam passage may have a length in the cross machine direction which is equal to or greater than a length of a side seam which is to be formed in the precursor web, or may have a length in the cross machine direction which is smaller than a length of a side seam which is to be formed in the precursor web if the laser beam passage is open at one or both ends such that the laser beam may continue outside the laser beam passage. The laser beam passage is arranged in registry with and overlying the side seam area on the outer periphery of the support roll, the laser beam being controlled to move along the laser beam passage in the cross machine direction and in the machine direction in synchrony with rotation of the support roll, while adapting a position of a focus point of the laser beam to a varying distance between the laser unit and the support surface;

cooling the side seams while continuing pressing the precursor web within the pressing areas of the leading and the trailing individual pant-type garments and moving the welded and severed individual pant-type garments along a cooling section arranged at the outer periphery of the support roll to a take-off section arranged at the outer periphery of the support roll;

releasing the pressure on the pressing areas and removing the individual pant-type garments from the support surface of the support roll.

In the method as disclosed herein, the focus point of the laser beam may be at 0 to 60 millimetres from the support surface of the support roll, such as at 20 to 40 millimetres from the support surface of the support roll or at 25 to 30 millimetres from the support surface of the support roll. A particularly suitable distance between the focus point of the laser beam and the support surface of the support roll may be in the range of from 25 to millimetres.

By moving the focus point away from the support surface of the support roll, and from the surface of the precursor web, a defocused, less distinct light incidence area is obtained. The laser beam passage is a narrow elongated passage, which may take the form of a slit through a press device such as a press clamp or a press belt or may be formed as a gap between two press elements. Generally, all the material in the side seam area of the precursor web is affected by the laser energy which impinges on the material exposed within the laser beam passage. A central portion of the beam provides enough energy to completely melt or evaporate material in the precursor web, thereby creating a side cut in the precursor web. Less energy is supplied at the peripheral portions of the beam causing the thermoplastic material in the precursor web to melt or soften and to fuse layers of the precursor web to each other thereby forming narrow fused side seams extending along the length of the laser beam passage on each side of the side cut.

The pressing arrangement keeps the precursor web firmly pressed down against the surface of the support roll along each longitudinal side of the seam area. The precursor web is held on the support roll while being stretched at least in the machine direction. Stretching of the precursor web during the welding and cutting step contributes to creating neat well-defined side seams having a generally rectangular or box-shaped cross-sectional area and a clean, well separated side cut.

The pressing arrangement keeps the superposed layers in the precursor web pressed together and contributes to ascertain that melted material from the different layers can fuse together and be consolidated into side seams having a generally rectangular or box-shaped cross-sectional area.

The pressing arrangement also prevents severed elastic elements and other elastic components from contracting the web material along the side seams, whereby damage to the side seams can be avoided.

The support roll may be a suction roll. A suction roll is hollow and has a perforated outer surface. The suction roll generates a suction force directed through the perforations towards the interior of the support roll and may contribute to holding the precursor web against the support surface. The suction roll may also contribute to remove fumes which are generated by evaporation of material in the welding section of the support roll during laser welding and cutting of a precursor web.

Feeding the precursor web onto the support surface of the support roll at the lay-down position may be carried out using a lay-down arrangement, such as a lay-down arrangement comprising or consisting of a deflection roll.

Removing the individual pant-type garments from the support surface of the support roll may be carried out using a take-off arrangement, such as a take-off arrangement comprising or consisting of a suction roll. The pant-type garments are preferably kept firmly pressed by the pressing arrangement to the support surface of the support roll until the severed pant-type garments have reached the take-off section. In this manner, the individual pant-type garments are prevented from contracting under the influence of any tensioned elastic material in the pant-type garments.

The precursor webs and the pant-type garments as disclosed herein may include any useful component or feature of a pant-type garment as known in the art. Such components and features may include leg elastic, waist features, side flaps, tape tabs, barrier cuffs, absorbent elements, barrier layers, wetness indicators, graphics, etc.

In the method as disclosed herein, the laser beam passage has a width as measured in the rotating direction of the support roll of from 1 to 5 millimetres, such as from 1 to 3 millimetres, from 1.5 to 2.5 millimetres or from 1.7 to 2.2 millimetres. As set out herein, the laser beam passage may be arranged in a press device of the pressing arrangement, such as a press clamp or a press belt or may be formed as a gap between two press elements, such as between two press bars. Furthermore, the laser beam passage may include an outer portion constituted by a narrow opening or slit in the pressing arrangement and a corresponding inner portion constituted by a narrow opening or slit in the support surface. The outer and inner portions of the laser beam passage are arranged in registry with each other such that they together form the laser beam passage. When a precursor web is placed between the pressing arrangement and the support surface, the outer and inner portions of the laser beam passage are arranged on opposite surfaces of the precursor web.

In the method as disclosed herein, at least two pressing arrangements, such as 2 to 8, or 3 to 5 pressing arrangements, may be arranged with a spacing between the pressing arrangements corresponding to a length of an individual pant-type garment as measured in the rotating direction along the support surface of the support roll, the pressing arrangements being moved together with the support roll in the rotating direction.

A pressing arrangement as used in the method disclosed herein may comprise a pivotable clamp, the pivotable clamp being movable between a pressing position in which the pivotable clamp is pressed down on the precursor web, and a release position in which the pivotable clamp is lifted up from the precursor web. The pivotable clamp is movable together with the precursor web in the rotating direction of the support roll. The laser beam passage may be arranged in the pivotable clamp, or may be formed between two pivotable clamps.

When lifted to the release position, the pivotable clamp or clamps may be arranged to extend radially in a direction perpendicular to the surface of the support surface of the support roll.

The pivotable clamp or pivotable clamps may be moved between the pressing position and the release position by means of a cam mechanism being arranged along a peripheral edge of the support roll and acting on a hinge arrangement arranged at an inner end of each pivotable clamp.

The laser welded side seams are allowed to cool and solidify while keeping pressure on the precursor web within the side seam areas of the leading and the trailing individual pant-type garments, during movement of the welded and severed individual pant-type garments along the cooling section to the take-off position.

The method as disclosed herein may further involve removing fumes generated when applying energy to the precursor web. The fumes may be removed by means of a fume removal arrangement located in an interior of the support roll, and/or at the support surface of the support roll on the outside of the support surface. The fume removal arrangement is configured to remove fumes which are generated in the welding section. When the support roll is a suction roll, the negative pressure generated inside the suction roll may contribute to remove fumes from the welding area.

The welded side seams may be allowed to cool by means of ambient air only as the severed pant-type garments are moved on the rotating support surface from the welding section to the take-off section. Cooling may be speeded up and controlled by means of a cooling arrangement located within the cooling section on the inside and/or on the outside of the support roll.

The laser beam which is used to create the side seams and to sever the precursor web is preferably generated by a laser unit which is configured and controlled to adapt the position of the focus point of the laser beam to a varying position in the cross machine direction and the machine direction and to a varying distance between the laser unit and the support surface of the support roll during movement of the precursor web through the welding section.

As set out herein, the laser unit is configured such that it can be controlled to move the laser beam along the laser beam passage in the pressing arrangement. As the support roll rotates through the welding area, the laser beam needs to move both in the cross machine direction of the support surface and in the machine direction in synchrony with the rotation of the support roll. In addition, the position of the focus point of the laser beam needs to be adapted to a varying distance between the laser unit and the support surface, such that the focus point is kept at a constant distance from the support surface throughout the welding and cutting operation.

The laser welding and cutting operation may be performed in a direction corresponding to a direction from a waist edge to a leg edge on the precursor web. Alternatively, the welding and cutting operation may be performed in a direction corresponding to a direction from a leg edge to a waist edge on the precursor web.

When the precursor web has travelled through the welding section, the laser beam has at the same time moved from one end of the laser beam passage to the other end of the laser beam passage. Under influence of the energy imparted to the precursor web during the course of the welding operation, a cut is formed along a cut line which is created by the moving focus point of the laser beam. The cut line may be straight or have any desired shape, such as a curved shape and may be off-set from the cross machine direction. The shape of the laser beam passage is preferably adapted to the shape of the desired cut line. However, if the deviation from a straight cut line is very small, such that it can be accommodated within the width of the laser beam passage, it may not be necessary to provide the laser beam passage with a shape corresponding to the shape of the cut line.

The focus point of the laser beam may be located on the support surface of the support roll, but is preferably located at a distance from the support surface in order to create a slight defocus of the laser beam and a larger incidence area on the precursor web.

The material in the precursor web is completely melted and/or evaporated along the cut line. In the portions of the side seam area which are located on either side of the cut line thermoplastic material in the precursor web is melted and/or softened such that narrow band-shaped fusion bonds are formed along inner edges of the laser beam passage, simultaneously creating one side seam on a leading pant-type garment and one side seam on a trailing pant-type garment. Fusion of the thermoplastic material in superposed layers of the precursor web is promoted by the pressure applied by the pressure arrangement along the edges of the side seam area. Without wishing to be bound to theory, it is also believed that the pressure applied along the edges of the side seam area contributes to promote a clean separation of the individual pant-type garments along the cut line. As set out herein, separation of individual garments may be further enhanced by stretching the precursor web in the machine direction MD while the precursor web is held on the support roll.

BRIEF DESCRIPTION OF THE DRAWINGS

The present invention will be further explained hereinafter by means of non-limiting examples and with reference to the appended drawings wherein:

FIG. 8 FIGS. 8*a*, 8*b* and 8*c* show a precursor web of pant-type garments during processing in an apparatus such as shown in FIG. 7;

DETAILED DESCRIPTION

It is to be understood that the drawings are schematic and that individual components, such as layers of material are not necessarily drawn to scale. The disposable pant-type absorbent garments shown in the figures are provided as examples only and should not be considered limiting to the invention as disclosed herein. As set out herein, the invention is applicable also to non-absorbent garments and reusable pant-type garments or garments which can be laundered and reused a limited number of times. Reusable garments which may withstand laundering may be non-absorbent pant-type garments e.g. pant-type garments which are adapted for use together with an absorbent insert.

Furthermore, the construction of the pant-type garments may be different from those shown in connection with the figures. As set out herein, an alternative construction of a unitary chassis may comprise a single continuous outer cover sheet, and/or a continuous inner liner and elastic panel webs joined to one or both of the front and back part of the chassis to form an elastic front or back panel, respectively.

Figure 1:
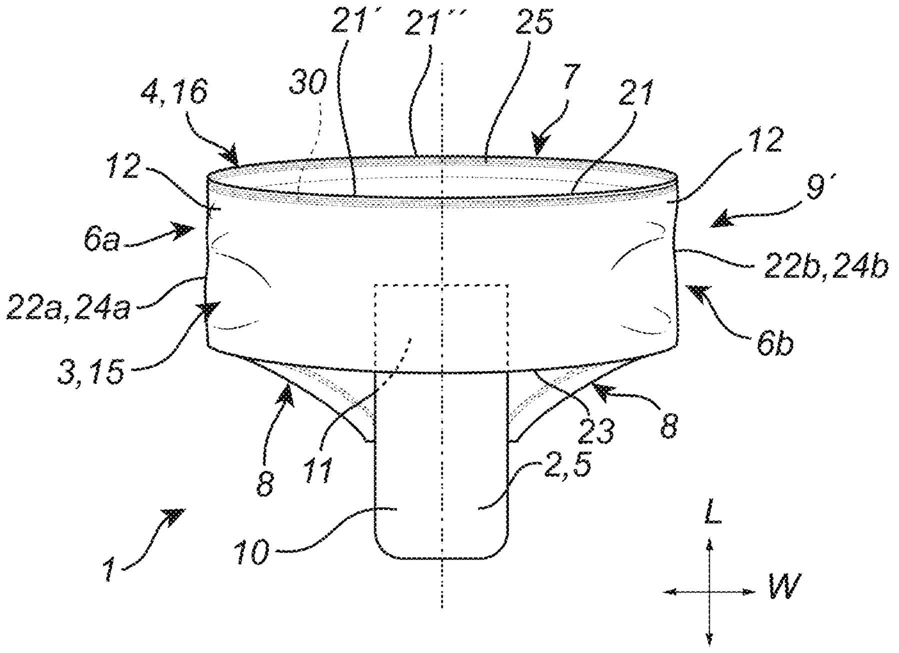
FIG. 1 shows a front view of an example pant-type garment with a two-part outer cover.
Figure 2:
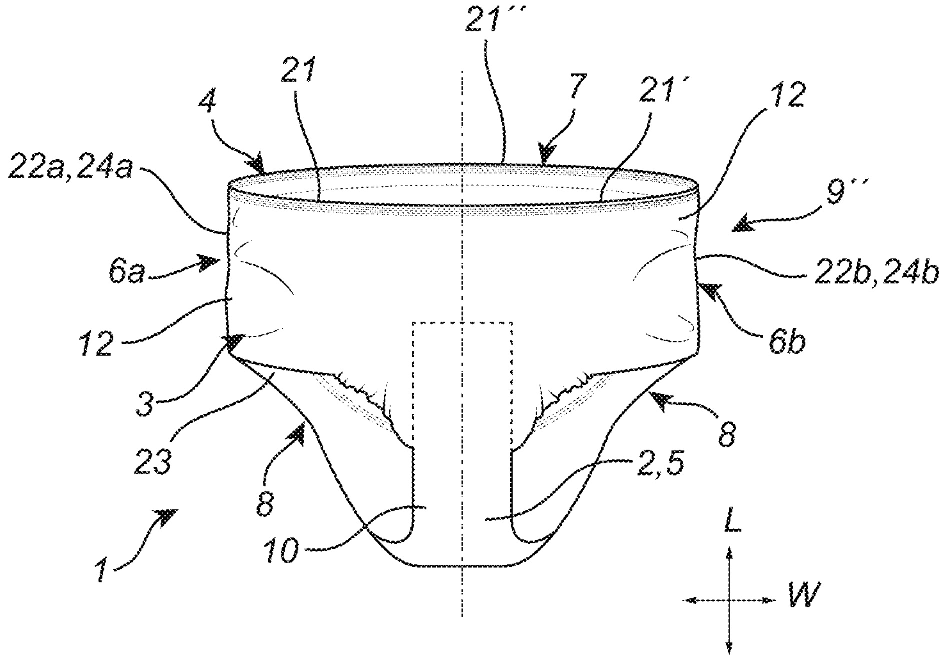
FIG. 2 shows a front view of an example pant-type garment with a unitary cover.

The pant-type garments shown in the figures are simplified garments, and it should be understood that they may be enhanced with elastic elements arranged at the leg openings on one or more of the front panel, the back panel and in the crotch portion. Further elastification may be provided e.g. in the form of barrier cuffs. It is also to be understood that the waist elastic disclosed in connection with FIGS. 1 and 2 is optional or that it may be substituted by any other type of elastic waist feature as known in the art. The pant-type garments 1 which are shown in FIGS. 1 and 2 are illustrated in an extended state similar to how they appear when extended to fit the lower trunk of a user.

The pant-type garment 1 shown in FIG. 1 has a longitudinal direction L and a width direction W and comprises a two-piece outer cover 9' forming a front panel 3 and a back panel 4 of the pant-type garment 1, the front and back panels 3, 4 being arranged at a front portion 15 and a back portion 16 of the pant-type garment 1. A core insert 2 is located mainly in a crotch portion 10 of the pant-type garment 1 between the front portion and the back portion 16 as seen in the longitudinal direction (L). The core insert 2 bridges a gap between the front and back portions 15, 16 and extends with end portions 11 in over the front and back portions 15, 16 and is connected at the end portions 11 to an interior side of the front and back portions 15, 16. The core insert 2 is a separately produced component which comprises an absorbent core 5 for absorbing body fluid. The front portion 15 has a front waist edge 21' and a pair of side edges 22*a*, 22*b*, and the back portion 16 has a back waist edge 21" and a pair of side edges 24*a*, 24*b*. The side edges 22*a*, 22*b*, 24*a*, 24*b* of the front and back portions 15, 16 are joined in side seams 6*a*, 6*b*, thereby forming the pant-type garment 1 having a waist opening 7 and two leg openings 8.

Figure 3:
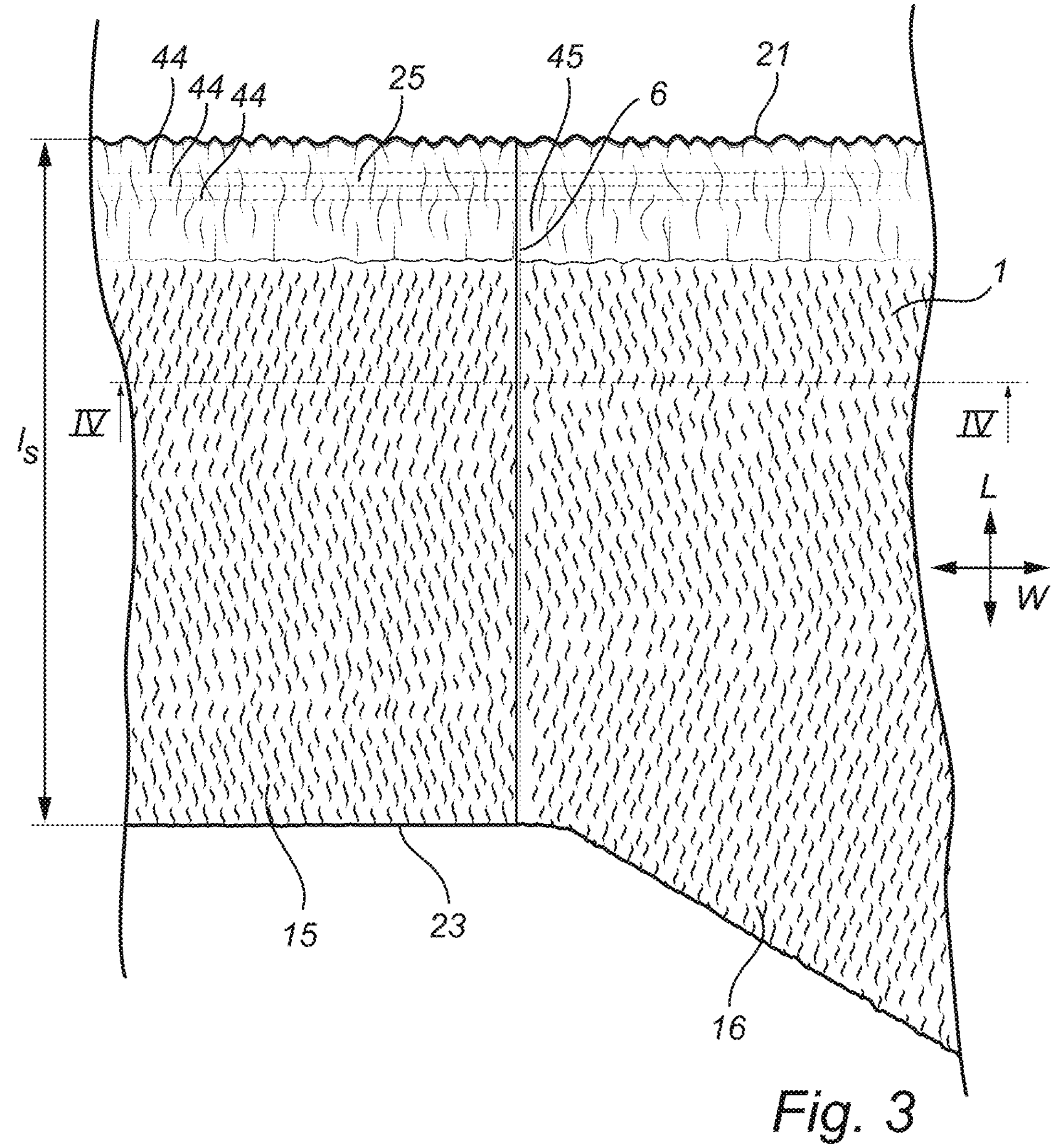
FIG. 3 shows a detail view of a side seam in a pant-type garment as disclosed herein.
Figure 4:
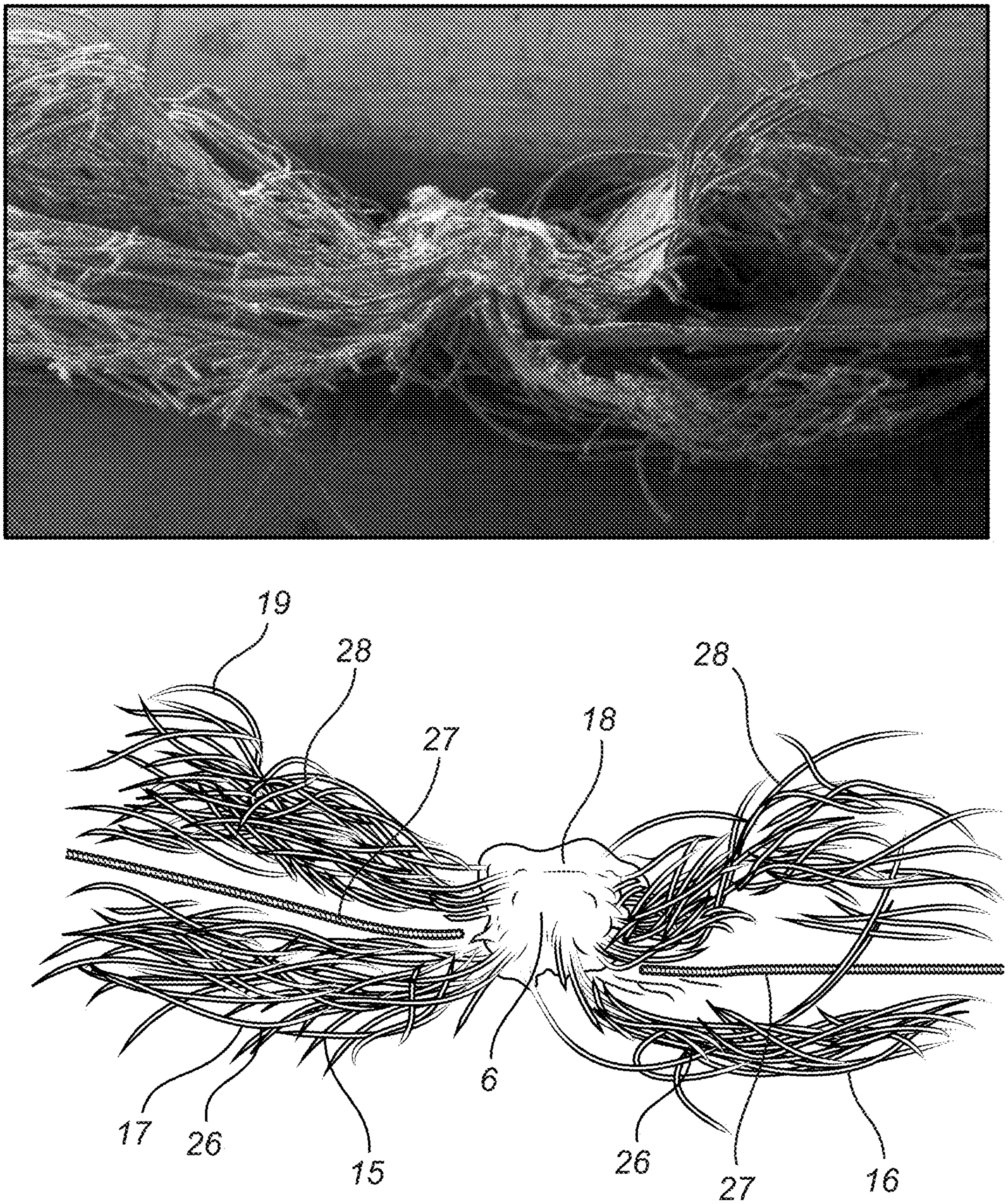
FIG. 4 shows a cross-section taken along the line IV-IV through the side seam in FIG. 3.

The side seams 6*a*, 6*b* are arranged in side seam regions 12 of the pant-type garment 1. The side seam regions 12 are the parts of the pant-type garment 1 which during use are placed over the hips of a user. Each side seam regions 12 extends between the waist opening 7 to a corresponding one of the leg openings 8 of the pant-type garment 1. As set out herein, the pant-type garment 1 comprises or consists of superposed webs within the side seam regions 12. As seen in FIGS. 3 and 4, the side seams 6*a*, 6*b* are formed as fused strips in web material which includes thermoplastic polymer material and which is arranged along the side edges 22*a*, 22*b*, 24*a*, 24*b* of the front and back portions 15, 16 of the the pant-type garment 1.

The pant-type garment 1 which is schematically shown in FIG. 1 is illustrated in an extended state and is fully assembled and ready-to-use. The pant-type garment 1 shown in FIG. 1 is an absorbent garment and may be a pant diaper, a sanitary pant or an incontinence pant and may be adapted for use of an adult female or male user.

The material in the back panel 4 may be the same or different from the material in the front panel 3. At least one of the front panel 3 and the back panel 4, and preferably both the front panel 3 and the back panel 4 are formed from a stretch bonded laminate web comprising a layer of elastic material, such as an elastic film layer which is sandwiched between two outer nonwoven layers. The bonding of the layers of the laminate web may be effected by means of an intermittent pattern of discrete bond elements as set out herein. Bonding may be made by any suitable method, with ultrasonic bonding being generally preferred.

FIG. 2 shows a second example of a pant-type garment 1, such as a garment for an adult female or male user. The pant-type garment 1 is schematically illustrated in an assembled and ready-to-use state. The difference between the pant-type garments in FIGS. 1 and 2 is that the pant-type garment 1 in FIG. 2 has a unitary outer cover 9", i.e. the front and back portions 15, 16 comprises a web material which is continuous at least in the longitudinal direction L of the pant-type garment 1 and which includes a crotch portion 10 interconnecting the front and back portions 15, 16, the crotch portion 10 being integrally formed with the front and back portions 15, 16. In the pant-type garment 1 in FIG. 2, there is no clear delimitation between the front portion 15, the crotch portion 10 and the back portion 16, while in FIG. 1 the crotch portion 10 is defined between the front and back panels 3,4.

The unitary outer cover 9" including the front portion 15, the back portion 16 and the interconnecting crotch portion 10 may preferably be fully or partly formed from a stretch bonded laminate web as disclosed herein and comprising a layer of elastic material, such as an elastic film layer which is sandwiched between two outer nonwoven layers.

At least one and preferably both of the front portion 15 and the back portion 16 in the examples of FIGS. 1 and 2 includes or consists of an elastic laminate web as disclosed herein such as a laminate of an elastic film sandwiched between two fibrous outer layers. The elastic laminate need not be identical all over its area, but may comprise different layers in different areas. In FIG. 1, the front portion 15 is coextensive with the front panel 3 and extends in the longitudinal direction L of the pant-type garment 1 from an upper part of a leg edge 23 to a waist edge 21 and in the width direction W from one side seam 6*a* to the other side seam 6*b*. The back portion 16 is coextensive with the back panel 4 and extends in the longitudinal direction L of the pant-type garment 1 from an upper part of a leg edge 23 to the waist edge 21 and in the width direction W from one side seam 6*a* to the other side seam 6*b*. As shown in FIG. 1, the front portion 15 and the back portion 16 of the pant-type garment as disclosed herein may be provided with a waist elastic feature 25 which may e.g. be in the form of supplementary elastic elements attached along the waist edge 21 of the pant-type garment 1, a separately produced elastic waistband attached along the waist edge 21 of the pant-type garment 1, or may be of any other suitable kind as set out herein.

The shape of the front and back portions 15, 16 may be varied to fit a particular category of user. For example, one or both of the front portion and the back portion 15, 16 may have a substantially rectangular shape. Moreover, a leg edge region of the front and/or back portions 15, 16 may have a curved shape adapted to provide better conformance to a leg. As is illustrated in FIGS. 1 and 2, the back panel portion 16 may have a greater extension in the longitudinal direction L of the pant-type garment than the front portion 15 in order to provide better coverage of the buttocks of a user. However, the front and back portions 15, 16 may have equal extensions in the longitudinal direction L. Although generally less preferred, the front portion 15 may have a greater extension in the longitudinal direction L of the pant-type garment 1 than the back portion 16.

With reference to FIGS. 3 and 4 there is shown a detail view of a side seam 6 connecting a front portion 15 and a back portion 16 of a pant-type article 1, e.g. a pant-type garment 1 as shown in FIGS. 1 and 2. The side seam 6 is formed by of fused thermoplastic material and has a length $l_s$ in the longitudinal direction L of the pant-type garment 1 from a waist edge 21 to a leg edge 23 of the pant-type garment 1 and a width $w_s$ in the width direction W of the pant-type garment 1. The side seam 6 extends in the length direction L across a waist elastic feature 25 which is arranged along the waist edge 21. As set out herein, the waist elastic feature 25 may be of any kind as known in the art. In the example shown in FIG. 3, the front and back portions 15, 16 are constituted by a three-layer elastic laminate 17 having an elastic film 27 bonded between an inner nonwoven web 26 and an outer nonwoven web 28. The waist elastic feature 25 is a waistband which has been created by attaching multiple spaced-apart elastic strings 44 on the outer nonwoven web and covering the elastic strings with a folded-over part 45 of the inner nonwoven web layer of the three-layer elastic laminate of the front and back portions 15, 16. Regardless of the type of waist elastic feature 25, a waist elastic feature extending into the side seam 6 means that material such as elastic elements and any covering or support layer would be present in the side seam. As in the FIG. 3 example, the waist feature materials are often present in addition to the materials forming the front and back portions 15, 16. It has been found that the presence in the side seam of such additional material does not significantly affect the side seam strength either positively or negatively.

In the example shown in FIGS. 3 and 4 the front portion 15 and the back portion 16 are both made from elastic web material forming an outer cover at least within the areas of a front panel 3 and a back panel 4 or within elastic side flaps. The elastic web material is a three-layer laminate 17 comprising an inner elastic film 27 which has been stretch-bonded between an outer and an inner nonwoven layer 28. The nonwoven layers 26, 28 are non-elastic or less elastic than the elastic film 27 and the elastic film layer 27 is bonded between the nonwoven layers 26, 28 while being stretched by at least 50% at least in a direction corresponding to the width direction W of the pant-type garment 1.

Bonding of the stretchbonded three-layer laminate is made by means of intermittently applied discrete bond elements as disclosed herein.

When the elastic laminate web is allowed to relax after bonding, the elastic film retracts, causing the non-elastic or less elastic nonwoven webs to gather and form wrinkles and rugosities on the outer surfaces of the elastic laminate web. The textile appearance of the outer surface of the elastic laminate web may be enhanced by using a bonding pattern which promotes formation of a regular pattern of rugosities. A particularly suitable bonding pattern may be a pattern of off-set point bonds which causes the gathered nonwoven webs to pucker in a controlled and regular way in the non-bonded portions between the point bonds. Such controlled puckering of the nonwoven webs may be made to resemble a woven pattern and provides the elastic laminate web with high-loft, soft and airy cushioning outer layers having a functional thickness which is considerably greater than the thickness of the non-gathered nonwoven webs. The point bonds may be created e.g. by thermobonding or by ultrasonic bonding, with ultrasonic bonding being preferred, as disclosed herein. It may be particularly preferred that the elastic film layer is a non-thermoplastic film and the nonwoven layers are thermoplastic layers or at least predominantly thermoplastic layers and that bonding of the elastic film layer between the nonwoven web layers is carried out by simultaneously perforating the elastic film layer and create fusion bonds between the nonwoven web layers at the perforations in the elastic film layer. An elastic laminate which has been made in this way has excellent breathability and is highly suitable for use as an outer cover in a pant-type garment as disclosed herein.

With reference to FIG. 4, it can be seen that the side seam 6 has the form of having a generally rectangular or box-shaped cross-sectional area $a_s$, as set out herein. The three-layer elastic laminate 17 in the front and back panels 3, 4 is shown in a gathered state as it would appear when being taken out of a package. The three-layer elastic laminate 17 will also be at least somewhat gathered during wearing of the pant-type garment. In this state, the inner and outer nonwoven layers 26, 28 of the three-layer elastic laminate 17 assume a puckered configuration, with an apparent thickness which is considerably greater than the thickness of the box-shaped side seam 6. The side seam 6 is arranged on the outer, garment-facing surface of the three-layer elastic laminate 17 of the front and back portions 15, 16 and has an outer surface 18 located a distance d inward of the outer surface 19 of the three-layer elastic laminate 17 of the front and back portions 15, 16. In this manner the relatively stiff consolidated material in the fused elongated side seam 6 is effectively shielded by the soft and lofty material in the front and back portions 15, 16. Furthermore, the rugosities in the three-layer elastic laminate also serve to conceal the side seam, making the side seam almost invisible to the naked eye when the garment is being worn.

Figure 5:
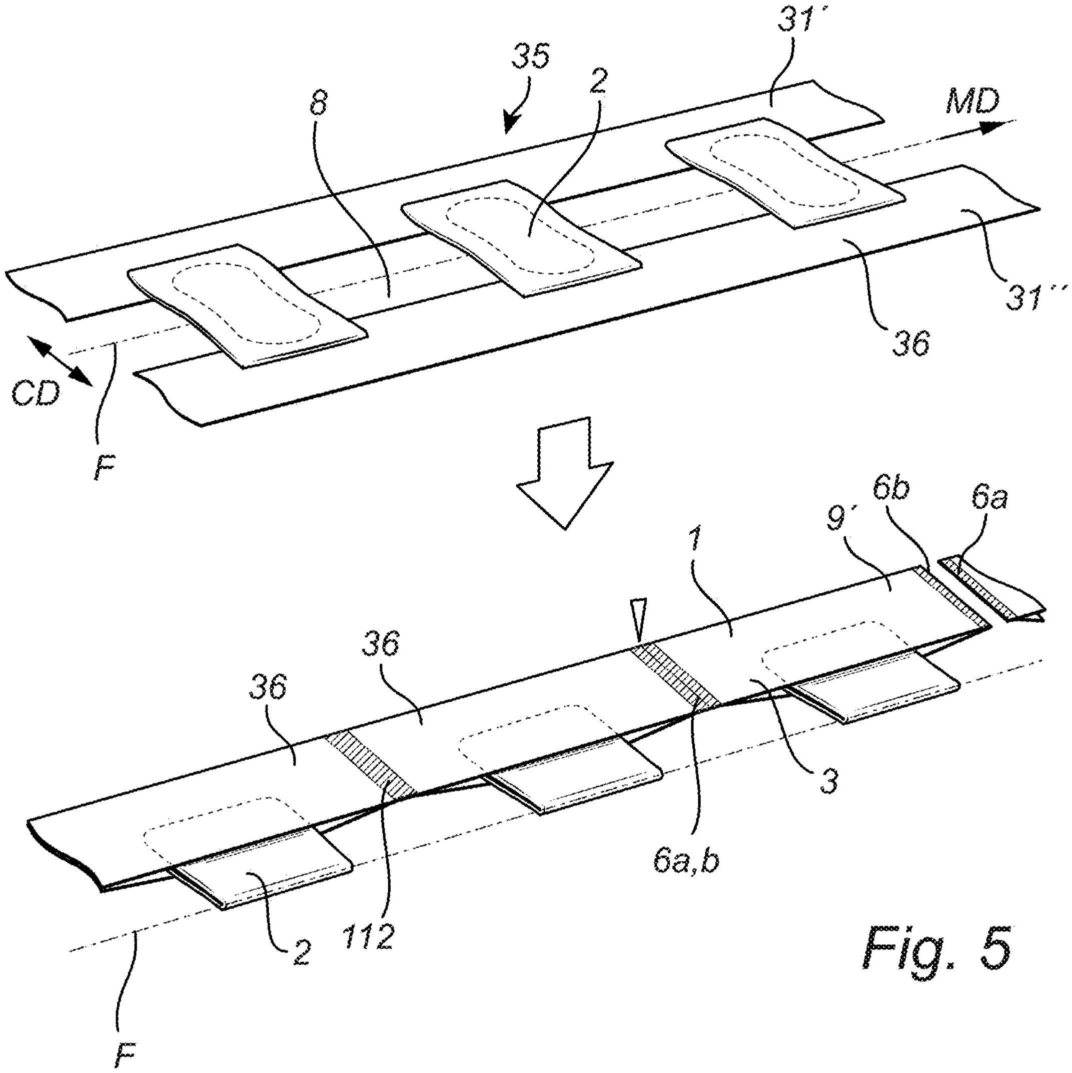
FIG. 5 shows a precursor web for a pant-type garment with a two-part outer cover.

FIG. 5 shows a precursor web 35 for forming pant-type garments 1 of the kind disclosed herein and having a two-piece outer cover 9', e.g. as illustrated in FIG. 1. The precursor web 35 may be formed by manufacturing two parallel continuous elastic laminate webs 31', 31", such as stretchbonded laminated elastic webs, and intermittently connecting the continuous elastic laminate webs 31', 31" with a crotch material, such as a core insert 2 while moving the precursor web 35 in a machine direction MD.

Depending on the desired shape of the leg openings of the pant-type garment 1, the web material may be cut and shaped to provide a more underwear-like shape and better fit of the pant-type garment 1.

A separately fabricated core insert 2 is placed in the gap between the elastic laminate webs 31', 31" while the webs 31', 31" are held in a tensioned state in the machine direction MD, such that the core insert 2 partly overlaps with both of the elastic laminate webs 31', 31". The absorbent insert 2 may be secured to the elastic laminate webs 31', 31" by any suitable method or combination of methods, such as by welding, thermobonding, by means of adhesive, etc.

The precursor web 35 is a continuous web having leg openings 8 arranged therein and consisting of interconnected precursor pant-type garments 36. As shown in FIG. 5, the precursor web 35 is folded along a fold line F, extending in the machine direction MD, centrally along the precursor web 35.

After the precursor web 35 has been folded, side seams **6*a*, 6*b* are formed in side seam areas 112 of the precursor web 35 and individual pant-type garments 1 are separated from the precursor web 35 by severing the precursor web at the same time as the side seams 6*a*, 6*b*** are formed.

Figure 6:
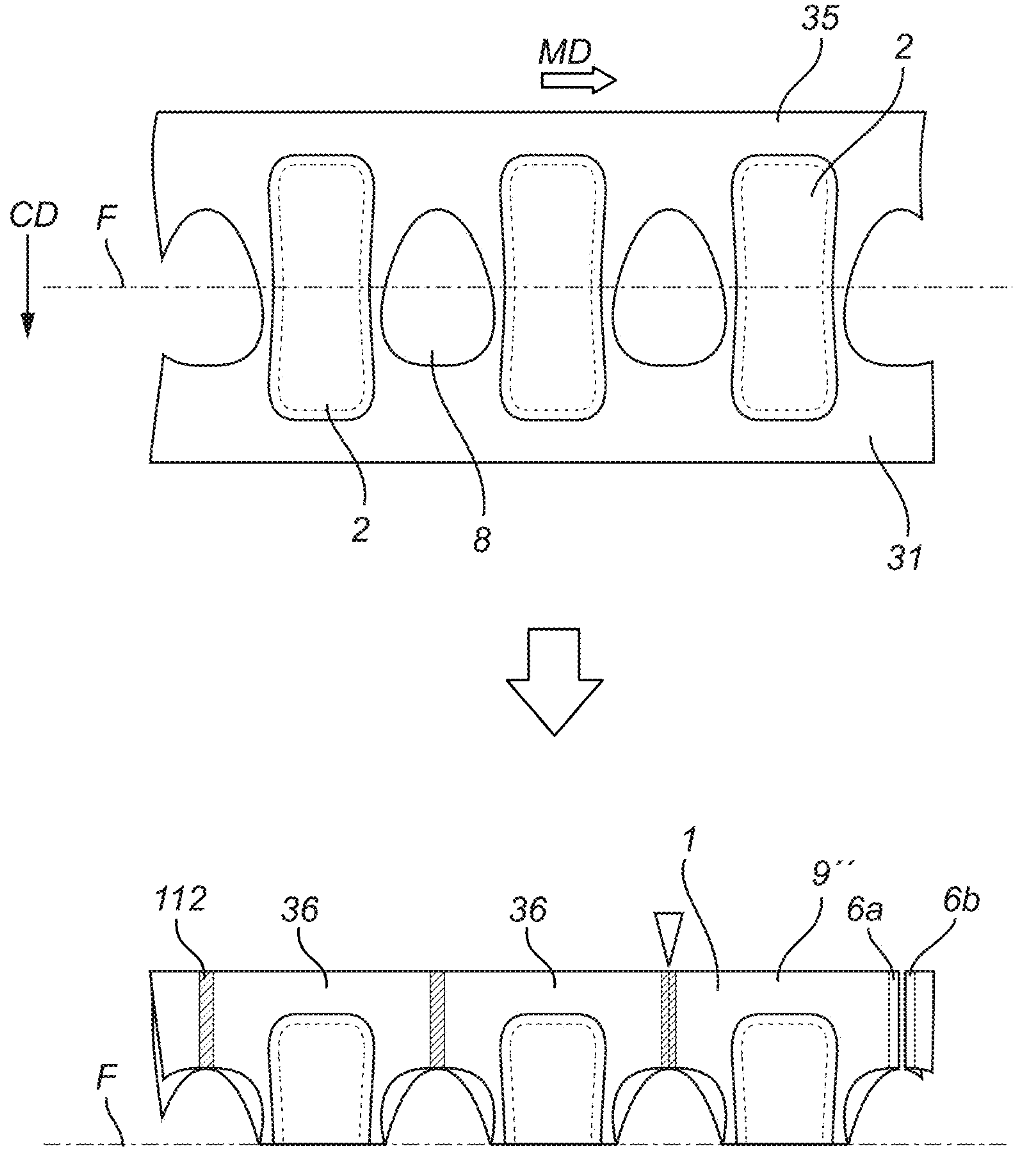
FIG. 6 shows a precursor web for a pant-type garment with a unitary cover.

The precursor web 35 which is illustrated in FIG. 6, is a continuous web of precursor pant-type garments 36 of the kind as disclosed herein and having a unitary outer cover, such as the pant-type garment 1, shown in FIG. 2. The precursor web 35 in FIG. 6 is formed by moving an elastic laminate web 31 in a machine direction MD; intermittently applying core inserts 2 to the moving elastic laminate web 31 and cutting out leg openings 8 between the core inserts 2. The precursor web 35 is subsequently folded along a fold line F extending in the machine direction, MD.

A precursor web of pant-type absorbent garments having a unitary cover may alternatively be produced by applying absorbent cores between moving continuous inner and outer cover webs, at least one of the cover webs having a width in the cross machine direction CD corresponding to a full length of the unitary cover. Furthermore, the precursor web may comprise components which are not shown in the figures, such as a barrier layer, an acquisition layer, leg elastic elements, etc., as known in the art.

After the precursor web 35 has been folded, side seams are formed in the folded precursor web 35 and individual pant-type garments 1 are separated from the precursor web 35 by severing the precursor web at the same time as forming side seams **6*a*, 6*b* between the precursor pant-type garments 36**.

It is to be understood that the elastic material in the elastic laminate web 31 needs not be continuous in the cross machine direction, CD. By way of example, the elastic material may be applied only in one or both of the areas of the elastic laminate web 31 corresponding to the front and back panels 3, 4 in the pant-type garment 1.

Figure 7:
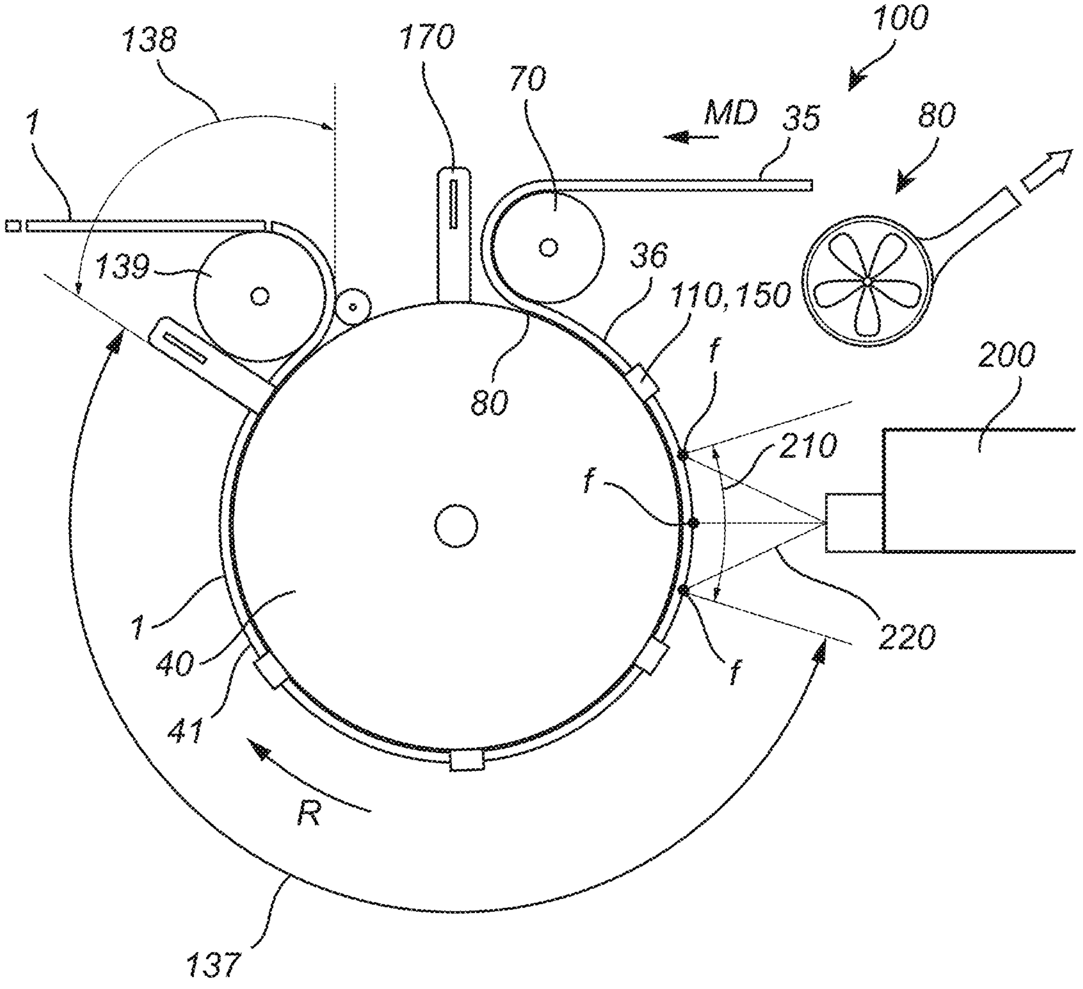
FIG. 7 shows a side view of an apparatus for simultaneously forming side seams and severing individual pant-type garments from a precursor web of interconnected pant-type garments.

FIG. 7 shows an apparatus 100 for simultaneously forming side seams and severing individual pant-type garments of the kind disclosed herein from a precursor web 35 of interconnected precursor pant-type garments 36. The apparatus comprises a support roll having an outer peripheral support surface 41 for supporting the precursor web 35 during formation of side seams and severing individual pant-type garments 1 from the precursor web 35. The support roll 40 has a rotating direction R coinciding with a machine direction MD of the apparatus 100. The apparatus further has a cross machine direction CD perpendicular to the machine direction MD and the rotating direction R of the support roll 40.

The apparatus 1 is provided with a lay-down arrangement 70. In FIG. 7, the lay-down arrangement is shown as a deflection roll which feeds the precursor web 35 in the machine direction MD onto the support surface 41 at a lay-down position 80 on the outer periphery of the support roll 40.

The precursor web 35 which may be separated into individual pant-type garments 1 may be a precursor web such as shown in FIGS. 3 and 4. The precursor web 35 is laid-down on the support surface 41 of the support roll 40 as a continuous web of interconnected pant-type garments 36. At the end of the laser welding and cutting operation as disclosed herein, individual pant-type garments 1 have been severed from the continuous precursor web 35 and can be removed and transported to folding and packaging equipment downstream of the welding and cutting apparatus 100.

The apparatus 100 is further provided with one or more pressing arrangements 110. The apparatus 1 which is shown in FIG. 7 has six pressing arrangements 110 equidistantly spaced along the outer periphery of the support roll 40. The number of pressing arrangements 110 is not critical to the apparatus or the method as disclosed herein, and it is to be understood that any useful number of pressing arrangements may be used, as set out herein. The spacing between the pressing arrangements 110 may preferably be selected to correspond to a pitch-length of the pant-type garments 1 in the machine direction MD.

Figures 8A, 8B, 8C:
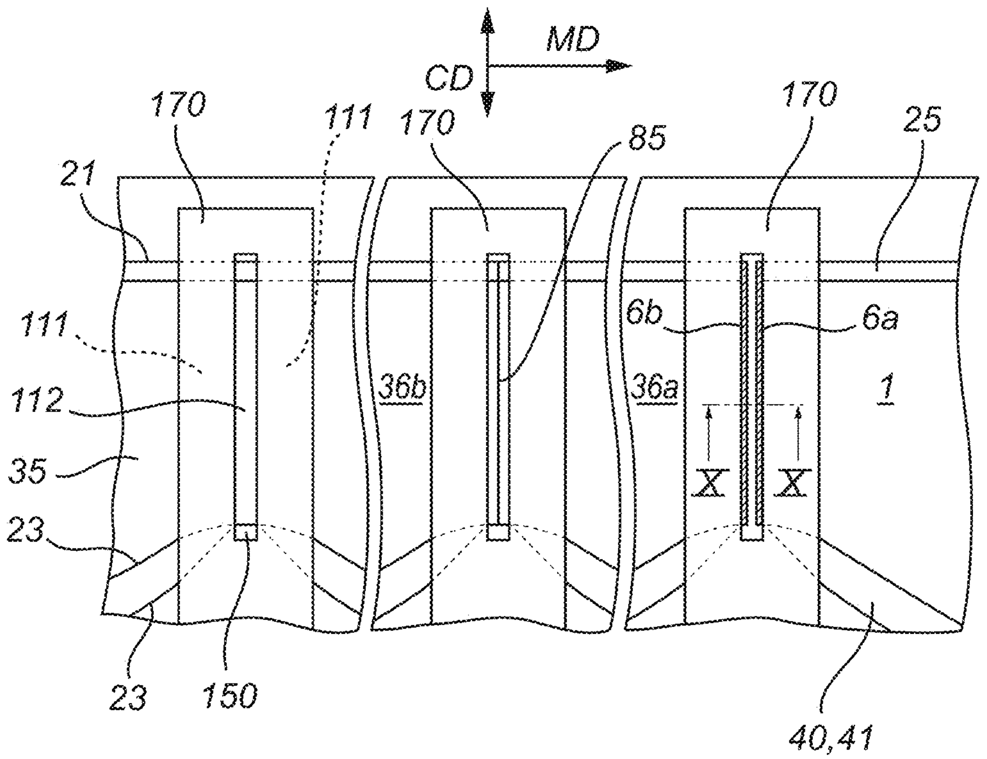

The pressing arrangement 110 is provided with pressing means, such as the press clamps 170 shown schematically in FIGS. 8*a*, 8*b*,8*c* and which are arranged for pressing the precursor web 35 against the support surface 41 within pressing areas 111 arranged on opposite sides of a side seam area 112 of a leading and a trailing individual pant-type garment 1*a*, 3*b*, as seen in the machine direction MD. The pressing areas 11 are located adjacent and along the side seam area 112. A laser beam passage 150 is arranged in the press clamp 170 between the pressing areas 111. The laser beam passage 150 is shown in FIGS. 3 and 4 as a narrow opening or slit in the press clamp 170. As set out herein, the laser beam passage 150 may alternatively be provided e.g. as a gap between spaced-apart pressing bars or as an opening in a pressing belt. The laser beam passage 150 has a length in the cross machine direction CD which is equal to or greater than a length of a side seam 6*a*, 6*b* which is to be formed in the precursor web 35. The press clamp 170 is applied to the precursor web with the laser beam passage 150 in registry with and overlying the side seam area 112 on the support surface 41 on the outer periphery of the support roll 40. Thereby, the side seam area 112 is completely accommodated within the laser beam passage 150.

Figure 9:
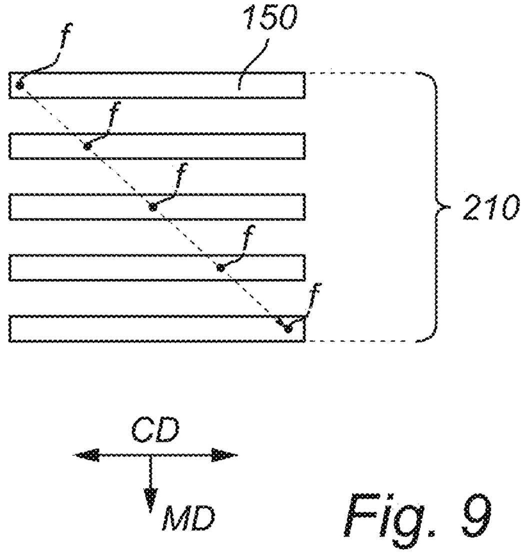
FIG. 9 shows the path of a laser beam during processing of a precursor web of pant-type garments when simultaneously forming side seams and severing individual pant-type garments from the precursor web of interconnected pant-type garments.

A laser unit 200 is arranged at a welding section 210 of the outer periphery of the support roll 40. The laser unit 200 is configured to direct a laser beam 220 through and along the laser beam passage 150 as shown in FIGS. 8*a*, 8*b*, 8*c*. The laser unit 200 is configured to generate the laser beam 220 and to move the focus point f of the laser beam 220 along the laser beam passage 150 from one end of the laser beam passage 150 to the other end of the laser beam passage 150 in the cross machine direction CD. As the support roll is continuously rotating, the focus point f must simultaneously be moved in the machine direction MD in synchrony with the rotation of the support roll 40, as is illustrated in FIG. 9. The focus point f should be kept at a constant distance from the support surface during movement of the laser beam 200 along the laser beam passage 150. As the laser unit 200 is stationary while the support roll 40 rotates in the machine direction MD and the laser beam 220 is moved across the support surface 41 in the cross machine direction CD, the distance between the laser unit 200 and the support surface 41 varies during the welding and cutting operation carried out in the welding section 210. The laser unit 200 is therefore also configured such that the position of the focus point f of the laser beam 220 is adapted to the varying distance between the laser unit 200 and the support surface 41.

As used herein, a laser unit which is configured to adapt the position of the focus point f of the laser beam comprises means e.g. a data processing unit which based on relevant in-data, such as rotational speed of the support roll, radius of the support roll, length and shape of the laser beam passage, etc. can out-put a control signal to change settings of the laser generating equipment in the laser unit.

FIGS. 8*a*, 8*b* and 8*c* show a part of the support roll 40 and the support surface 41 with a precursor web 35 pressed against the support surface 41 by a press clamp 170 which is part of a pressing arrangement 110. Only the part of the support surface 41 and the precursor web 35 where side seams 6*a*, 6*b* are to be formed is shown in FIGS. 8*a*, 8*b* and 8*c*. The upper part of FIGS. 8*a*, 8*b* and 8*c* shows a waist edge 21 and a waist elastic feature 25 while the lower part of FIGS. 8*a*-8*c* show an upper part of the leg edges 23 of the pant-type garments 1 in the precursor web 35.

FIGS. 8*a*, 8*b* and 8*c* illustrate how side seams 6*a*, 6*b* are formed in the precursor pant-type garments 36*a*, 36*b* at the same time as individual pant-type garments 1 are severed from the precursor web 35. By applying laser energy to the precursor web 35 through the laser beam passage 150, thermoplastic material in superposed layers of the precursor web is locally melted and fused within the side seam area 112, and at the same time, the precursor web 35 is severed to separate individual pant-type garments from the precursor web 35. The laser beam 220 is directed through and along the laser beam passage 150 from outside the support roll 40, which makes the laser unit 200 and the pressing arrangements 110 easily accessible for maintenance and replacement. Furthermore, a fume removal arrangement 80 may be provided on the outside of the support roll 40, preferably such that fumes generated by the welding and severing process can be removed directly from the welding section 210 of the support roll 40.

As set out herein the laser beam 220 is controlled to move along the laser beam passage 150 in the cross machine direction CD of the support surface 41 and in the machine direction MD in synchrony with rotation of the support roll 40, while adapting the position of the focus point f of the laser beam 220 to a varying distance between the laser unit and the support surface 41, such that the focus point f is kept at a constant distance from the support surface 41.

FIG. 9 shows how the focus point f of the laser beam 220 moves both in the cross machine direction CD and in the machine direction MD as the laser beam passage 150 in the clamping arrangement 110 moves through the welding section 210 and the side seams 6*a*, 6*b* are formed. FIG. 9 shows the focus point f moving from the left-hand side of the laser beam passage 150 to the right-hand side of the laser beam passage 150 which may be taken to correspond to the welding process being performed from a waist edge 21 to a leg edge 23 on the precursor web 35. It is to be understood that it is equally viable to form the side seams 6*a*, 6*b* in the opposite direction, i.e. from right to left in FIG. 9 corresponding to the side seams being formed from a leg edge 23 to a waist edge 21 on the precursor web 35.

When the precursor web 35 has travelled through the welding section 210 and the laser beam has acted on the precursor web 35, a cut is formed along a cut line 85 as is shown in FIG. 8*b*. The cut line 85 is created by the moving focus point f of the laser beam 220. The focus point f of the laser beam 220 may be located on the support surface 41 of the support roll 40, but is preferably located at a distance from the support surface 41 in order to create a slight defocus of the laser beam and a larger incidence area on the precursor web 35. A laser beam having the focus point f at a distance from the support surface 41 of from 25 to 35 millimetres has been found to provide a particularly useful combination of good side seam strength and a distinct cut between the side seams. However, the focus point f of the laser beam may be at 0 to 60 millimetres from the support surface of the support roll, such as at 20 to 40 millimetres from the support surface of the support roll, or at 25 to 30 millimetres from the support surface of the support roll.

The material in the precursor web 35 is completely melted and/or evaporated along the cut line 85. In the portions of the side seam area 112 which are located on either side of the cut line 85 thermoplastic material in the precursor web 35 is melted and/or softened such that narrow band-shaped fusion bonds are formed along the inner edges of the laser beam passage 150, creating one side seam 6*a* on a leading precursor pant-type garment 36*a* and one side seam 6*b* on a trailing precursor pant-type garment 36*b*. Fusion of the thermoplastic material in superposed layers of the precursor web 35 is promoted by the pressure applied by the pressure means such as the press clamps 170 of the pressure arrangement at the very edges of the side seam area 112. Without wishing to be bound to theory, it is also believed that the pressure applied along the edges of the side seam area 112 contributes to promote separation of the individual pant-type garments 36*a*, 36*b* along the cut line 85, as is shown in FIG. 8*c*. Separation of individual garments 1 is further enhanced by stretching the precursor web 35 in the machine direction MD while the precursor web 35 is held on the support roll 40.

Figure 10:
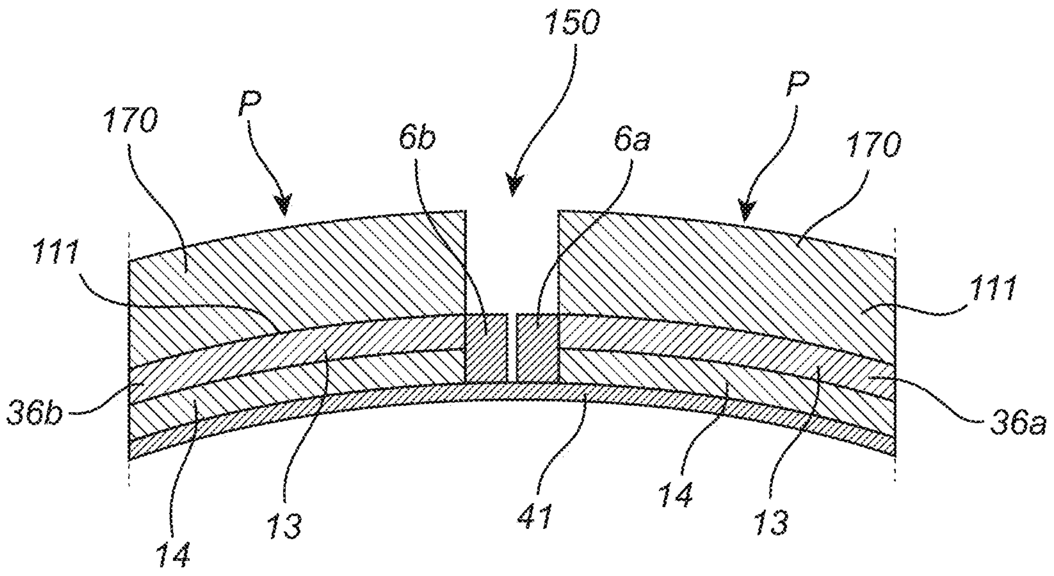
FIG. 10 shows a cross section taken along the line X-X in FIG. 8*c;*

FIG. 10 is a cross-section taken along the line X-X in FIG. 8*c* and shows the newly formed and separated side seams 6*a*, 6*b* of a leading and a trailing precursor pant-type garment 36*a*, 36*b*. The superposed layers of the front panel web 13 and the back panel web 14 of the precursor garments 36*a*, 36*b* are pressed down on the support surface 41 by means of the press clamps 170 (or other pressing means) exerting a pressure force P on the pressing areas 111 immediately adjacent the side seams 6*a*, 6*b*.

Immediately after the side seams 6*a*, 6*b* have been formed in the welding section 210 of the apparatus 100 shown in FIG. 7, the fused thermoplastic material is still hot and soft and needs to be cooled down and solidify to create strong functional side seams 6*a*, 6*b*.

In order for the side seams 6*a*, 6*b* to solidify, the severed precursor web 35 is transported along a cooling section 137 of the support roll 40. When moving through the cooling section 137, the severed precursor web 35 is held pressed to the support surface 41 by the pressing arrangement 110. By keeping the pressure P on the severed precursor web 35, any tensioned elastic in the precursor web 35 is prevented from contracting and causing damage to the newly formed side seams 6*a*, 6*b*. Cooling of the severed precursor web 35 may be carried out by exposure to ambient air only. It is also conceivable to use a cooling arrangement such as cooled air, or cooling elements arranged in the support roll within the cooling section 137.

At the end of the cooling section 137, the severed and cooled precursor web 35 reaches a take-off section 138 with a take-off arrangement 139. The take-off arrangement 139 is shown in FIG. 7 as a rotating suction roll. The take-off arrangement 139 is configured to remove individual pant-type garments 1 from the support roll 40. When the individual pant-type garments 1 have been separated from the precursor web 35, any elastic material such as elastic laminate webs, waist elastic and leg elastic in the pant-type garments 1 is no longer held in a stretched state. Thereby, the elastic will cause the pant-type garments 1 to gather, i.e. to contract and form rugosities or wrinkles in non-elastic or less elastic web material which is bonded to the elastic components.

EXAMPLES

Tested Material

The tested materials were ultrasonic bonded elastic materials having outer spunbond propylene nonwoven layers having a basis weight of 16 gsm (grams per square meter) and an elastic film of an ethylene based copolymer from Exten SA (Extretch MD2) The film was stretched to a stretch ratio of approximately 1:3 and bonded with ultrasonic bonds to outer nonwoven layers having a bond area of about 5%.

Test

Figure 11:
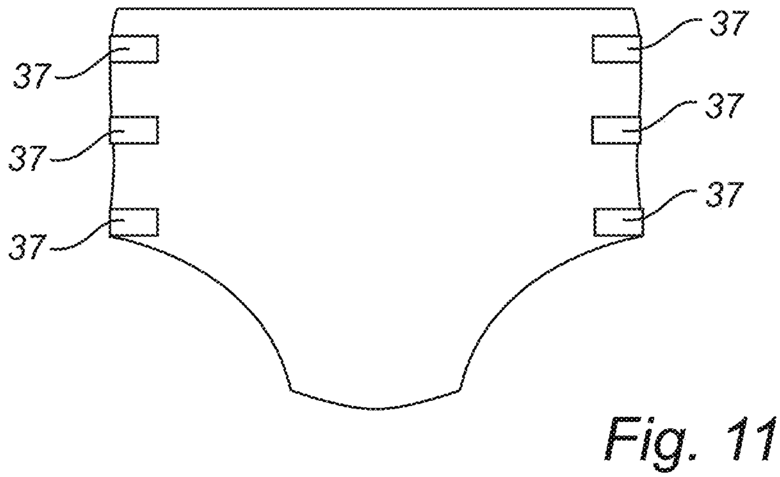
FIG. 11 shows schematically where samples may be cut out from a pant-type garment.

Sample width 25 mm, sample length adapted to product to be tested. Samples 37 were taken across the side seam on the left and the right side of the pant-type garment, as illustrated by FIG. 11.

Equipment

Tensile tester Instron 5965 with System ID 5965L3520

Software criteria for programming of break:

Crosshead speed: 300 mm/min

A break is detected when the load drops to 0.02 N or when it drops to 5% of the maximum load.

Load with 2 s delay or detector becomes active at 1 N.

Load cell within the measurement test area. If unsure, always start with a high max load cell of at least 100 N.

Results: Maximum load, Type of break

The width of the plates of the clamps: 25 mm. The clamps must be as wide as or wider than the sample width.

Distance between clamps: around 25-50 mm

Cutter with rotating knife or punching tool.

When punching, punch templates of 25 mm in width, the length might vary due to which product to be tested.

Sample Preparation

Punch or cut out test strips from desired parts of the side seams, making sure that the elastics are stretched before the samples are punched by using a stretching plate. Make sure not to overstretch the product.

Procedure

Start up and zero/balance the tensile tester. See apparatus instruction.

Set the distance between the clamps.

Make sure the load is zero before every sample is mounted in the tensile tester.

Figure 12:
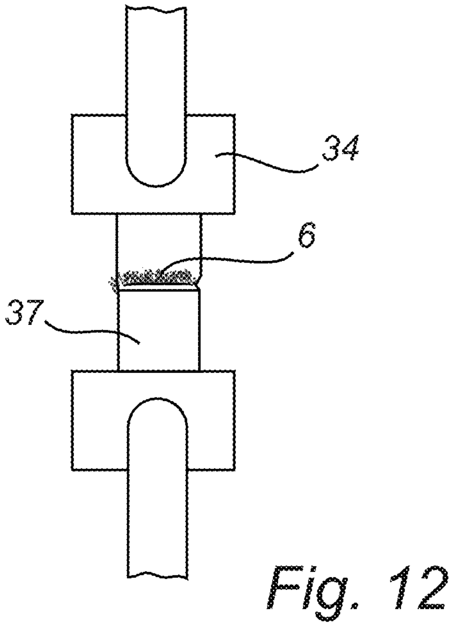
FIG. 12 shows a sample fastened between two claps in a tensile tester.

Fasten the test strip 37 with the side seam 6 of fused material between the clamps 34 in the tensile tester, according to FIG. 12.

Start the pulling.

Stop when the layers have separated.

Note the maximum value=F (N) and if it there was a break in the sealing or in the materials outside the sealing.

TABLE 1

Side seam strength test data

| Waist right (N/25/mm) | Waist left (N/25/mm) | Middle right (N/25/mm) | Middle left (N/25/mm) |
|---|---|---|---|
| 21.82 | 25.14 | 25.82 | 23.44 |
| 22.53 | 20.89 | 28.12 | 26.31 |
| 21.09 | 23.3 | 24.57 | 31.22 |
| 26.18 | 25.51 | 25.07 | 22.31 |
| 25.76 | 18.18 | 23.29 | 23.08 |

TABLE 1-continued

| Side seam strength test data | | | | |
|---|---|---|---|---|
| | Waist right (N/25/mm) | Waist left (N/25/mm) | Middle right (N/25/mm) | Middle left (N/25/mm) |
| Average: | 23.5 | 22.6 | 25.4 | 25.3 |
| Stdev: | 2.3 | 3.1 | 1.8 | 3.7 |

Test Method Material Thickness

Principle

Thickness is defined as the dimension between two surfaces of an object, all materials included. The thickness is determined by means of a measuring foot with a fixed load which is lowered onto the sample at a given rate. The thickness is read off at the digital thickness gauge/tester after 5 seconds when the measuring foot has touched the surface of the sample.

Equipment

Thickness gauge/tester, model DT-25 supplied by IM-Teknik AB, Reningsverksgatan 6, 421 47 Västra Frölunda, accuracy ±0.03 mm.

TABLE 2

| Square measuring foot | |
|---|---|
| Area | 20 $cm^2$ (45 mm × 45 mm) |
| Foot weight: | 103 g |
| Force | 1.0 N/20 $cm^2$ = 0.05 $N/cm^2$ |
| Speed | 13 mm/s ± 1 mm/s |

For stretching of the samples a stretching equipment was used with a first, stationary clamp and a second clamp, the second clamp being movable within a frame such that the sample can be stretched in a longitudinal direction between the clamps. A force measuring device was attached to the movable clamp to measure the load force. The force measuring device may e.g. be a dynamometer.

Sample Preparation

Handle the products carefully when determining thickness to receive comparable results. Cut out a sample perpendicular to the side seam. A pair of scissors or a punch tool can be used. The sample should be 50 mm wide and minimum 150 mm long.

Procedure

Unfold the front panel and the back panel from each other and fix the ends in the stretching clamps. Stretch the sample till 10 N. (at this load the material was stretched to about 100% i.e. the stretch ratio 1:2)

Place the intended measuring surface under the measuring foot. The outer, garment-facing nonwoven layer should be arranged facing upwards towards the measuring foot.

Lower the measuring foot and when the foot touches the surface of the product wait 5 seconds but not longer before reading the result on the display.

Note! Avoid measure over folds and wrinkles.

Thickness Test Results

Ten comparable samples were cut across a welded seam between two pieces of the tested material and the material thickness and the seam thickness were measured. The average material thickness of the samples was 0.7 millimeters with a standard deviation of 0.09. The average seam thickness of the samples was 0.73 millimeters with a standard deviation of 0.07. The ratio $t_s/t_m$ between the seam thickness $t_s$ and the material thickness $t_m$ was determined to be 1.06 with a standard deviation of 0.15.

Figure 13:
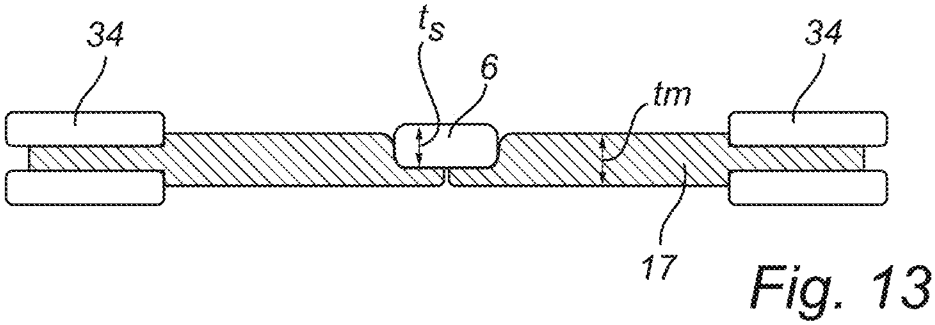
FIG. 13 shows a stretched-out sample for measuring of thickness.

Hence, the seam thickness $t_s$ as determined by the thickness of the side seam 6 was found to be slightly greater than the material thickness $t_m$ of the adjoining material 17 and to protrude somewhat from the garment-facing surface of the stretched tested samples as illustrated by FIG. 13 where a sample is shown attached between two clamps 34.

The invention claimed is:

1. A pant-type garment having a longitudinal direction and a width direction and being divided in the longitudinal direction into a front portion, a back portion and a crotch portion located between the front portion and the back portion, the front portion having a front waist edge extending in the width direction and a pair of opposing side edges extending in the longitudinal direction and the back portion having a back waist edge extending in the width direction and a pair of opposing side edges extending in the longitudinal direction, the front and back portions comprising an elastic laminate comprising an elastic film which is stretch-bonded between two outer nonwoven webs comprising thermoplastic material, the elastic film being coextensive with a majority of the two outer nonwoven webs, the front and back portions being joined in a first and a second side seam arranged in first and second side seam regions formed by superposed layers of the front and back portions along the opposing side edges of the front and back portions, the side seams being fully or partly formed in the elastic laminate, the side seams comprising fused portions of the thermoplastic material extending along the side edges of the front and back portions of the pant-type garment, wherein each of the side seams has a width in the width direction of the pant-type garment in the range of from 0.3 to 1.5 millimetres, and a thickness in the range of from 0.2 to 1.5 millimeters, the thickness of the side seam being perpendicular to the width direction and the longitudinal direction of the pant type garment, wherein the elastic film is severed along the side seams in the longitudinal direction forming a non-elastic area extending in the width direction from each side of each of the side seams and extending in the longitudinal direction for at least a majority of a length of each of the side seams.

2. A pant-type garment having a longitudinal direction and a width direction and being divided in the longitudinal direction into a front portion, a back portion and a crotch portion located between the front portion and the back portion, the front portion having a front waist edge extending in the width direction and a pair of opposing side edges extending in the longitudinal direction and the back portion having a back waist edge extending in the width direction and a pair of opposing side edges extending in the longitudinal direction, the front and back portions comprising an elastic laminate comprising an elastic film which is stretch-bonded between two outer nonwoven webs comprising thermoplastic material, the elastic film being coextensive with a majority of the two outer nonwoven webs, the front and back portions being joined in a first and a second side seam arranged in first and second side seam regions formed by superposed layers of the front and back portions along the opposing side edges of the front and back portions, the side seams being fully or partly formed in the elastic laminate, the side seams comprising fused portions of the thermoplastic material extending along the side edges of the front and back portions of the pant-type garment, wherein each of the side seams has a width in the width direction of the pant-type garment in the range of from 0.3 to 1.5 millimetres, and a thickness in the range of from 0.2 to 1.5 millimeters, the thickness of the side seam being perpendicular to the width direction and the longitudinal direction of the pant type garment, wherein the elastic film is intermittently bonded to the outer nonwoven webs with a bonding pattern comprising discrete bonding elements.

3. A pant-type garment according to claim 2, wherein a bonded area of the elastic laminate is from 3% to 20%.

4. A pant-type garment according to claim 1, wherein the elastic laminate has a material thickness and wherein a ratio $t_s/t_m$ between the thickness of the side seam and the material thickness is in the range of from 1.0 to 1.3, as measured by the method as disclosed herein.

5. A pant-type garment according to claim 1, wherein the non-elastic area has a width in the width direction on each side of each of the side seams of from 0.7 millimetres to 20 millimetres and extends in the longitudinal direction along 60% to 100% of the length of each of the side seams.

6. A pant-type garment according to claim 1, wherein the side seams are located on a garment facing surface of the pant-type garment.

7. A pant-type garment according to claim 1, wherein a ratio of the width of the side seams to the thickness of the side seams is in the range of from 0.7 to 1.5.

8. A pant-type garment according to claim 1, wherein each side seam has a generally rectangular cross-sectional area along 60% to 100% of the length of the side seams in the longitudinal direction of the pant-type garment.

9. A pant-type garment according to claim 1, wherein the elastic laminate constitutes a cover material, the cover material forming all or part of an outer cover of the pant-type garment.

10. A pant-type garment according to claim 9, wherein the cover material is a single, unitary cover web comprising a front portion, a back portion and a crotch portion between the front portion and the back portion.

11. A pant-type garment according to claim 9, wherein the cover material comprises a front panel web and a back panel web the front panel web and the back panel web being separate webs and being joined by a crotch material.

12. A pant-type garment according to claim 1, wherein at least one nonwoven web which is involved in forming the sides seams of the pant-type garment comprises at least one spunbond layer and optionally at least one meltblown layer.

13. A pant-type garment according to claim 1, wherein the thermoplastic material in the areas of the side seams comprises or consists of polypropylene and/or polyethylene.

14. A pant-type garment according to claim 1, wherein the pant-type garment comprises a waist elastic feature extending along all or part of one or both of the front waist edge and the back waist edge.

15. A pant-type garment according to claim 1, wherein the non-elastic area has a width in the width direction on each side of each of the side seams of from 0.9 millimetres to 5 millimetres and extends in the longitudinal direction along 80% to 100% of the length of each of the side seams.

16. A pant-type garment according to claim 1, wherein a ratio of the width of the side seams to the thickness of the side seams is in the range of from 0.9 to 1.2.

17. A pant-type garment according to claim 1, wherein the elastic laminate has a material thickness and wherein a ratio $t_s/t_m$ between the thickness of the side seam and the material thickness is in the range of from 1.1 to 1.3.

18. A pant-type garment according to claim 1, wherein the elastic laminate has a material thickness and wherein a ratio $t_s/t_m$ between the thickness of the side seam and the material thickness is in the range of from 1.1 to 1.2.

19. A pant-type garment according to claim 2, wherein a bonded area of the elastic laminate is from 3% to 15%.

20. A pant-type garment according to claim 2, wherein a bonded area of the elastic laminate is from 4% to 10%.

21. A pant-type garment according to claim 1, wherein the elastic film extends through an entirety of the front and back portions.

22. A pant-type garment according to claim 1, wherein the elastic film is continuous with a majority of the two outer nonwoven webs.

23. A pant-type garment according to claim 2, wherein the elastic film has perforations.

* * * * *